(12) United States Patent
Yoon

(10) Patent No.: US 9,382,316 B2
(45) Date of Patent: Jul. 5, 2016

(54) HUMANIZED ANTI-EMAP II ANTIBODY AND USE THEREOF

(75) Inventor: Kang-Jun Yoon, Seoul (KR)

(73) Assignees: Cell & Bio Co., Ltd., Seoul (KR); L & K Biomed Co., Ltd., Seoul (KR); Hee Koung Kim, Seoul (KR); Sang Gyu Park, Seoul (KR)

(*) Notice: Subject to any disclaimer, the term of this patent is extended or adjusted under 35 U.S.C. 154(b) by 140 days.

(21) Appl. No.: 14/113,209

(22) PCT Filed: Jul. 14, 2011

(86) PCT No.: PCT/KR2011/005203
§ 371 (c)(1),
(2), (4) Date: Dec. 20, 2013

(87) PCT Pub. No.: WO2012/144692
PCT Pub. Date: Oct. 26, 2012

(65) Prior Publication Data
US 2014/0154245 A1    Jun. 5, 2014

(30) Foreign Application Priority Data
Apr. 20, 2011    (KR) .................. 10-2011-0036569

(51) Int. Cl.
| | | |
|---|---|---|
| C07K 16/00 | (2006.01) | |
| C07K 16/46 | (2006.01) | |
| C07K 16/24 | (2006.01) | |
| C12P 21/06 | (2006.01) | |
| C12N 1/20 | (2006.01) | |
| C12N 15/00 | (2006.01) | |
| C07H 21/04 | (2006.01) | |
| C12N 15/87 | (2006.01) | |
| A61K 39/395 | (2006.01) | |
| C07K 16/18 | (2006.01) | |

(52) U.S. Cl.
CPC ............ C07K 16/24 (2013.01); C07K 16/18 (2013.01); C07K 2317/24 (2013.01)

(58) Field of Classification Search
None
See application file for complete search history.

(56) References Cited

U.S. PATENT DOCUMENTS

| | | | | |
|---|---|---|---|---|
| 4,275,149 A | 6/1981 | Litman et al. | ................ | 435/7.91 |
| 4,485,045 A | 11/1984 | Regen et al. | .................... | 554/80 |
| 4,544,545 A | 10/1985 | Ryan et al. | ................... | 424/1.21 |
| 4,737,456 A | 4/1988 | Weng et al. | ................... | 435/7.92 |
| 4,816,567 A | 3/1989 | Cabilly et al. | ............... | 53/387.3 |
| 5,013,556 A | 5/1991 | Woodle et al. | ................. | 424/450 |
| 5,641,867 A | 6/1997 | Stern et al. | ............... | 530/388.23 |
| 2011/0028349 A1 | 2/2011 | Dave et al. | ..................... | 506/18 |
| 2011/0250701 A1* | 10/2011 | Kim | ..................... | G01N 33/564 436/501 |
| 2014/0154245 A1 | 6/2014 | Yoon | ......................... | 424/133.1 |

FOREIGN PATENT DOCUMENTS

| | | |
|---|---|---|
| KR | 10-2010-0093451 | 8/2010 |
| WO | WO 96/07321 | 3/1996 |
| WO | WO 97/38731 | 10/1997 |
| WO | WO2010093214 | * 8/2010 |

OTHER PUBLICATIONS

Hong et al. The antibody atliximab attenuates collagen-induced arthritis by neutralizing AIMP1, an inflammatory cytokine that enhances osteoclastogenesis. Biomaterials 44 (2015) 45e54.*
Yuan et al. Blockade of EMAP II protects cardiac function after chronic myocardial infarction by inducing angiogenesis. J Mol Cell Cardiol. Feb. 2015;79:224-31.*
Clarijs et al. EMAP-II expression is associated with macrophage accumulation in primary uveal melanoma. (Invest Ophthalmol Vis Sci. May 2003;44(5):1801-6).*
Kwon et al. Identification of CD23 as a functional receptor for the proinflammatory cytokine AIMP1/p43. Journal of Cell Science 125, 4620-4629, 2012.*
Letter/Written Disclosure of the Information Disclosure Statemtn for the above-referenced application, mailed on Mar. 12, 2014, 2 pages.
Behrensdorf et al., "The endothelial monocyte-activating polypeptide II (EMAP II) is a substrate for caspase-7," FEBS Lett. 466:143-147 (2000).
Berger et al., "Endothelial monocyte-activating polypeptide II, a tumor-derived cytokine that plays an important role in inflammation, apoptosis, and angiogenesis," J. Immunother., 23:519-527 (2000).
Carter et al., "Humanization of an anti-p185HER2 antibody for human cancer therapy," Proc. Natl. Acad. Sci. USA, 89:4285-4289 (1992).
Chothia, C. and A. Lesk, "Canonical structures for the hypervariable regions of immunoglobulins," J. Mol. Biol., 196:901-917 (1987).
Deninger et al., "Aberrant neuronal and paracellular deposition of endostatin in brains of patients with Alzheimer's disease," J. Neurosci. 22(24):10621-10626 (2002).
English Language translation of Korean Patent Pub. No. 10-2010-0093451 (Korean Patent App. No. 10-2009-0054875), 34 pages.
Epstein et al., "Biological activity of liposome-encapsulated murine interferon gamma is mediated by a cell membrane receptor," Proc. Natl. Acad. Sci. USA 82:3688-3692 (1985).
Gabizon et al., "Pharmacokinetics and tissue distribution of doxorubicin encapsulated in stable liposomes with long circulation times," J. National Cancer Inst. 81 (19) 1484-1488 (1989).
Hwang et al., "Hepatic uptake and degradation of unilamellar sphingomyelin/cholesterol liposomes: a kinetic study," Proc. Natl Acad. Sci. USA 77:4030-4034 (1980).
Jones et al., "Replacing the complementarity-determining regions in a human antibody with those from a mouse," Nature 321:522-525 (1986).

(Continued)

Primary Examiner — Maher Haddad
(74) Attorney, Agent, or Firm — Dentons US LLP; Stephanie Seidman

(57) ABSTRACT

The present invention provides a humanized anti-EMAP II antibody, the use of the humanized antibody, and pharmaceutical compositions containing the humanized antibody. The humanized anti-EMAP II antibody shows reduced immunogenicity and increased half-life while having similar or improved antigen binding capacity compared to the parent monoclonal antibody. Thus, the humanized anti-EMAP II antibody of the present invention can be more effectively used as a diagnostic reagent for EMAP II and a therapeutic agent for diseases that are mediated by EMAP II.

20 Claims, 16 Drawing Sheets

(56) References Cited

OTHER PUBLICATIONS

Kao et al., "A peptide derived from the amino terminus of endothelial-monocyte-activating polypeptide II modulates mononuclear and polymorphonuclear leukocyte functions, defines an apparently novel cellular interaction site, and induces an acute inflammatory response," J. Biol. Chem. 269:9774-9782 (1994).

Kao et al., "Characterization of a novel tumor-derived cytokine. Endothelial-monocyte activating polypeptide II," J. Biol. Chem., 269:25106-25119 (1994).

Kao et al., "Endothelial monocyte-activating polypeptide II. A novel tumor-derived polypeptide that activates host-response mechanisms," J. Biol. Chem. 267:20239-20247 (1992).

Knies et al., "Regulation of endothelial monocyte-activating polypeptide II release by apoptosis," PNAS USA, 95:12322-12327 (1998).

Martin et al., "Irreversible coupling of immunoglobulin fragments to preformed vesicles. An improved method for liposome targeting," J. Biol. Chem. 257: 286-288 (1982).

O'Sullivan et a., "Methods for the preparation of enzyme-antibody conjugates for use in enzyme immunoassay," Methods in Enzym., (eds. J. Langone & H.Van Vunakis), Academic press, New York, 73:147-166 (1981).

Park et al., "Precursor of pro-apoptotic cytokine modulates aminoacylation activity of tRNA synthetase," J. Biol. Chem. 274:16673-16676 (1999).

Presta et al., "Humanization of an antibody directed against IgE," J. Immunol., 151:2623-2632 (1993).

Presta, L., "Antibody engineering ," Curr. Op. Struct. Biol., 2:593-596 (1992).

Quevillon et al., "The p43 component of the mammalian multi-synthetase complex is likely to be the precursor of the endothelial monocyte-activating polypeptide II cytokine," J. Biol. Chem. 272:32573-32579 (1997).

Riechmann et al., "Reshaping human antibodies for therapy," Nature, 332:323-327 (1988).

Schluesener et al., "Localization of endothelial-monocyte-activating polypeptide II (EMAP II), a novel proinflammatory cytokine, to lesions of experimental autoimmune encephalomyelitis, neuritis and uveitis: expression by monocytes and activated microglial cells," Glia, 20:365-372 (1997).

Schwarz et al., "Endothelial-monocyte-activating polypeptide II, a novel antitumor cytokine that suppresses primary and metastatic tumor growth and induces apoptosis in growing endothelial cells," J. Exp. Med. 190:341-353 (1999).

Sims et al., "A humanized CD18 antibody can block function without cell destruction," J. Immunol., 151:2296-2308 (1993).

Tas, M. and J. Murray, "Endothelial-monocyte-activating polypeptide II," Int. J. Biochem. Cell. Biol., 28:837-841 (1996).

Verhoeyen et al., "Reshaping human antibodies: grafting an antilysozyme activity," Science 239:1534-1536 (1988).

Zhang et al., "Early infiltration of CD8+ macrophages/microglia to lesions of rat traumatic brain injury," Neuroscience 141(2):637-644 (2006).

Zhang et al., "Microglia activation in rat spinal cord by systemic injection of TLR3 and TLR7/8 agonists," J. Neuroimmunology 164(1-2):154-160 (2005).

Zola, H., "Using Monoclonal antibodies: soluble antigens," Chapter 6 in *Monoclonal Antibodies: A Manual of Techniques*, CRC Press, Inc.: Boca Raton, FL, pp. 147-158 (1987).

International Search Report, issued Jun. 13, 2012, in connection with International Patent Application No. PCT/KR2011/005203, 6 pages.

International Preliminary Report on Patentability, issued Oct. 22, 2013, in connection with International Patent Application No. PCT/KR2011/005203, 8 pages.

Letter/Written Disclosure of the Information Disclosure Statement for the above-referenced application, mailed on Mar. 23, 2016, 2 pages.

English language translation of Park et al., "Effect of Antibody Against Inflammatory Cytokine in Dementia Syndrome," Journal of Korean Society of Geriatric Neurosurgery, 5(1):13-18 (2009), 8 pages.

Park et al., "Effect of Antibody Against Inflammatory Cytokine in Dementia Syndrome," Journal of Korean Society of Geriatric Neurosurgery, 5(1):13-18 (2009) [Document in Korean with English language abstract].

\* cited by examiner

PCR products obtained with kappa specific combinations

M: DNA maker (smallest fragment 500 bp)

Lanes 1.11: PCR with primer combinations mK1-mL11

PCR products obtained with heavy chani specific primer combinations

M: DNA maker (smallest fragment 500 bp)
Lanes 1.7: PCR with primer combinations mH1-mH7
Lane 8: control PCR mouse GAPDH

Figure 5

```
                    10        20        30        40        50        60
                ....|....|....|....|....|....|....|....|....|....|....|....|
     AAA39004   DIVLTQSPASLAVSLGQRATISYRASKSVSTSGYSYMHWNQQKPGQPPRLLIYLVSNLES

K2-1-T7    NIVLTQSPASLAVSLGQRATISYRASKSVSTSGYSYMHWNQQKPGQPPRLLIYLVSNLES
     K2-2-T7    DIVLTQSPASLAVSLGQRATISYRASKSVSTSGYSYMHWNQQKPGQPPRLLIYLVSNLES
     K2-3-T7     IVLTQSPASLAVSLGQRATISYRASKSVSTSGYSYMHWNQQKPGQPPRLLIYLVSNLES
     K2-4-T7     IVLTQSPASLAVSLGQRATISYRASKSVSTSGYSYMHWNQQKPGQPPRLLIYLVSNLES
     K2-5-T7    DIVLTQSPASLAVSLGQRATISYRASKSVSTSGYSYMHWNQQKPGQPPRLLIYLVSNLES
     K2-6-T7    DIVLTQSPASLAVSLGQRATISYRASKSVSTSGYSYMHWNQQKPGQPPRLLIYLVSNLES
     K3-2-T7    ENVLTQSPASLAVSLGQRATISYRASKSVSTSGYSYMHWNQQKPGQPPRLLIYLVSNLES
     K3-4-T7    ENVLSQSPASLAVSLGQRATISYRASKSVSTSGYSYMHWNQQKPGQPPRLLIYLVSNLES
     K3-5-T7    ENVLTQSPASLAVSLGQRATISYRASKSVSTSGYSYMHWNQQKPGQPPRLLIYLVSNLES
     K3-6-T7    ENVLTQSPASLAVSLGQRATISYRASKSVSTSGYSYMHWNQQKPGQPPRLLIYLVSNLES 70        80        90       100
                ....|....|....|....|....|....|....|....|....
     AAA39004   GVPARFSGSGSGTDFTLNIHPVEEEDAATYYCQHIRELTRSEGGPSWK*

K2-1-T7    GVPARFSGSGSGTDFTLNIHPVEEEDAATYYCQHIRELTRSEGGPSWK*
     K2-2-T7    GVPARFSGSGSGTDFTLNIHPVEEEDAATYYCQHIRELTRSEGGPSWK*
     K2-3-T7    GVPARFSGSGSGTDFTLNIHPVEEEDAATYYCQHIRELTRSEGGPSWK*
     K2-4-T7    GVPARFSGSGSGTDFTLNIHPVEEEDAATYYCQHIRELTRSEGGPSWK*
     K2-5-T7    GVPARFSGSGSGTDFTLNIHPVEEEDAATYYCQHIRELTRSEGGPSWK*
     K2-6-T7    GVPARFSGSGSGTDFTLNIHPVEEEDAATYYCQHIRELTRSEGGPSWE*
     K3-2-T7    GVPARFSGSGSGTDFTLNIHPVEEEDAATYYCQHIRELTRSEGGPSWK*
     K3-4-T7    GVPARFSGSGSGTDFTLNIHPVEEEDAATYYCQHIRELTRSEGGPSWK*
     K3-5-T7    GVPARFSGSGSGTDFTLNIHPVEEEDAATYYCQHIRELTRSEGGPSWK*
     K3-6-T7    GVPARFSGSGSGTDFTLNIHPVEEEDAATYYCQHIRELTRSEGGPSWK*
```

Figure 6

```
                     10        20        30        40        50        60
              ....|....|....|....|....|....|....|....|....|....|....|....|
Vk19-17       DIVMTQSHKFMSTSVGDRVSITCKASQDVSTAVAWYQQKPGQSPKLLIYSASYRYTGVPD
K6-2          S....T......................................F...............
K6-5          S...........................................F...............
K7-3          S.....P.....................................F...............
K7-6          N.....TP....................................F...............
K8-1          G...........................................F...............
K8-2          .......T....................................F...............
K9-1          G.....TP....................................F...............
K9-5          ......TP....................................F...............
K11-1         ..M...P.....................................F...............
K11-3         E.K...P.....................................F...............
K11-4         E.M...P.....................................F...............
K11-5         ...K...P....................................F...............
```

```
                     70        80        90        100
              ....|....|....|....|....|....|....|....|....|..
Vk19-17       RFTGSGSGTDFTFTISSVQAEDLAVYYCQQHYSTP~~~~~~~~~~~~
K6-2          .................................YTFGGGTKLEIK
K6-5          .................................YTFGGGTKLEIK
K7-3          .................................YTFGGGTKLEIK
K7-6          .................................YTFGGGTKLEIK
K8-1          .................................YTFGGGTKLEIK
K8-2          .................................YTFGGGTKLEIK
K9-1          .................................YTFGGGTKLEIK
K9-5          .................................YTFGGGTKLEIK
K11-1         .................................YTFGGGTKLEIK
K11-3         .................................YTFGGGTKLEIK
K11-4         .................................YTFGGGTKLEIK
K11-5         .................................YTFGGGTKLEIK
```

Figure 7

PCR of variable domains with gene specific primers

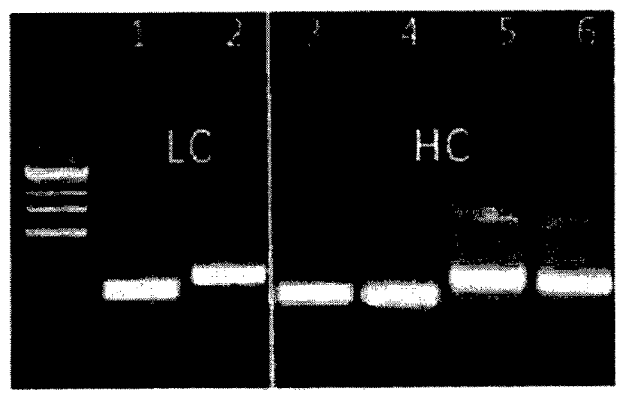

M: DNA maker (smallest fragment 500 bp)
Lane 1: LC PCR product primers annealing to secretion signal and CDR3
Lane 2: LC PCR product primers annealing to secretion signal and kappa constant region
Lane 3: HC PCR product primers annealing to secretion signal and CD3
Lane 4: HC PCR product primers annealing to 5' and of variable domain and CDR3
Lane 5: HC PCR product primers annealing to secretion signal and HC constant domain
Lane 6: HC PCR product primers annealing to 5' and of variable domain and HC constant domain

Figure 8

```
      D  I  V  M  T  Q  S  H  K  F  M  S  T  S  V  G  D  R  V  S
1     GACATTGTGATGACCCAGTCTCACAAATTCATGTCCACATCAGTAGGAGACAGGGTCAGC
      CTGTAACACTACTGGGTCAGAGTGTTTAAGTACAGGTGTAGTCATCCTCTGTCCCAGTCG
```

```
                               CDR L1
      I  T  C  K  A  S  Q  D  V  S  T  A  V  A  W  Y  Q  Q  K  P
61    ATCACCTGCAAGGCCAGTCAGGATGTGASTACTGCTGTAGCC TGGTATCAACAGAAACCA
      TAGTGGACGTTCCGGTCAGTCCTACACTCATGACGACATCGG ACCATAGTTGTCTTTGGT
```

```
                                CDR L2
      G  Q  S  P  K  L  L  I  F  S  A  S  Y  R  Y  T  G  V  P  D
121   GGACAATCTCCTAAACTACTGATTTTCTCGGCATCCTACCGGTACACT GGAGTCCCTGAT
      CCTGTTAGAGGATTTGATGACTAAAAGAGCCGTAGGATGGCCATGTGACCTCAGGGACTA
```

```
      R  F  T  G  S  G  S  G  T  D  F  T  F  T  I  S  S  V  Q  A
181   CGCTTCACTGGCAGTGGATCTGGGACGGATTTCACTTTCACCATCAGCAGTGTGCAGGCT
      GCGAAGTGACCGTCACCTAGACCCTGCCTAAAGTGAAAGTGGTAGTCGTCACACGTCCGA
```

```
                                CDR L3
      E  D  L  A  V  Y  Y  C  Q  Q  H  Y  S  T  P  Y  T  F  G  G
241   GAAGACCTGGCAGTTTATTACTGTCAGCAACATTATAGTACTCCGTACACGTTCGGAGGG
      CTTCTGGACCGTCAAATAATGACAGTCGTTGTAATATCATGAGGCATGTGCAAGCCTCCC
```

```
      G  T  K  L  E  I  K
301   GGGACCAAGCTGGAAATAAAA
      CCCTGGTTCGACCTTTATTTT
```

Figure 9

```
                    10        20        30        40        50        60
              ....|....|....|....|....|....|....|....|....|....|....|....|
mVh14 - 3*2   EVQLQQSGAELVKPGASVKLSCTASGFNIKDTYMHWVKQRPEQGLEWIGRIDPANGNTKY
H4 - 4        .WM.VE......................................................
H4 - 5        ..M.VE.E.....................................................
H4 - 6        ..M.VE.......................................................

70        80        90       100       110       120
              ....|....|....|....|....|....|....|....|....|....|....|....|
mVh14 - 3*2   DPKFQGKATITADTSSNTAYLQLSSLTSEDTAVYYCAR
H4 - 4        ....................................T.RGLL*VRRPCLLGPRDSGHCLC
H4 - 5        ....................................T.RGLL*VRRPCLLGPRDSGHCLC
H4 - 6        ....................................T.RGLL*VRRPCLLGPRDSGHCLC
```

Figure 10

```
                        10        20        30        40        50        60
                ....|....|....|....|....|....|....|....|....|....|....|....|
mVH1-4*1        QVQLQQSGAELARPGASVKMSCKASGYTFTSYTMHWVKQRPGQGLEWIGYINPSSGYTKY
H1-1            .......P..............A...................................F.N.
H1-2            A......F..................................................F.N.
H1-3            E......L..................................................F.N.
H2-4            P....KE...................................................F.N.
H3-1            ~~~.....F.................................................F.N.
H3-2            ~~~.....L.................................................F.N.
H3-4            ~~~.......................................................F.N.
H5-2            E....LET..................................................F.N.
H5-3            E....LET..................................................F.N.
H6-1            E.......V.................................................F.N.
H6-3            E.......V.................................................F.N.
H7-4            ..H.......................................................FAN.
H7-6            ..H....A..................................................F.N.
```

```
                        70        80        90       100       110       120
                ....|....|....|....|....|....|....|....|....|....|....|....|
mVH1-4*1        NQKFKDKATLTADKSSSTAYMQLSSLTSEDSAVYYCAR
H1-1            .....................................SRFAYWGQGTLVTVSAAKTTPPS
H1-2            .....................................SRFAYWGQGTLVTVSAAKTTPPS
H1-3            ...................P.................SRFAYWGQGTLVTVSAAKTTPPS
H2-4            .....................................SRFAYWGQGTLVTVSAAKTTPPS
H3-1            .....................................SRFAYWGQGTLVTVSAAKTTPPS
H3-2            .....................................SRFAYWGQGTLVTVSAAKTTPPS
H3-4            .....................................SRFAYWGQGTLVTVSAAKTTPPS
H5-2            .....................................SRFAYWGQGTLVTVSAAKTTPPS
H5-3            .....................................SRFAYWGQGTLVTVSAAKTTPPS
H6-1            .....................................SRFAYWGQGTLVTVSAAKTTPPS
H6-3            .....................................SRFAYWGQGTLVTVSAAKTTPPS
H7-4            .....................................SRFAYWGQGTLVTVSAAKTTPPS
H7-6            .....................................SRFAYWGQGTLVTVSAAKTTPPS
```

Figure 11

```
          Q   V   Q   L   Q   Q   S   G   A   E   L   A   R   P   G   A   S   V   K   M
  1   CAGGTCCAGCTGCAGCAGTCTGGGGCTGAACTGGCAAGACCTGGGGCCTCAGTGAAGATG
      GTCCAGGTCGACGTCGTCAGACCCCGACTTGACCGTTCTGGACCCCGGAGTCACTTCTAC

CDR H1
          S   C   K   A   S   G   Y   T   F   T   S   Y   T   M   H   W   V   K   Q   R
 61   TCCTGCAAGGCTTCTGGCTACACCTTTACTAGCTACACGATGCAC TGGGTAAAACAGAGG
      AGGACGTTCCGAAGACCGATGTGGAAATGATCGATGTGCTACGTG ACCCATTTTGTCTCC

CDR H2
          P   G   Q   G   L   E   W   I   G   Y   I   N   P   S   S   G   F   T   N   Y
121   CCTGGACAGGGTCTGGAATGGATTGGA TACATTAATCCTAGCAGTGGTTTTACTAATTAC
      GGACCTGTCCCAGACCTTACCTAACCT ATGTAATTAGGATCGTCACCAAAATGATTAATG

CDR H2
          N   Q   K   F   K   D   K   A   T   L   T   A   D   K   S   S   S   T   A   Y
181   AATCAGAAGTTCAAGGAC AAGGCCACATTGACTGCAGACAAATCCTCCAGCACAGCCTAC
      TTAGTCTTCAAGTTCCTG TTCCGGTGTAACTGACGTCTGTTTAGGAGGTCGTGTCGGATG

CDR H3
          M   Q   L   S   S   L   T   S   E   D   S   A   V   Y   Y   C   A   S   R   F
241   ATGCAACTGAGCAGCCTGACATCTGAGGACTCTGCAGTCTATTACTGTGCAAGT CGGTTT
      TACGTTGACTCGTCGGACTGTAGACTCCTGAGACGTCAGATAATGACACGTTCA GCCAAA

CDR H3
          A   Y   W   G   Q   G   T   L   V   T   V   S   A   A   K   T   T   P   P   S
301   GCTTAC TGGGGCCAAGGGACTCTGGTCACTGTCTCTGCAGCCAAAACGACACCCCCATCT
      CGAATGACCCCGGTTCCCTGAGACCAGTGACAGAGACGTCGGTTTTGCTGTGGGGGTAGA
```

| 4 - P Fit: y = (A - D) / ( 1 + (x /C) ^B ) + D: | A | B | C | D | R^2 |
|---|---|---|---|---|---|
| ○ Mouse (murine anti-P43: ng/ml vs AvgOD) | 0.0317 | 1.07 | 20.9 | 1.88 | 1 |
| ◇ Chimera 3 (MAP015-1/3: ng/ml vs AvgOD) | -0.00162 | 1.12 | 27.8 | 2.66 | 1 |
| ▲ Chimera 2 (MAP015-1/2: ng/ml vs AvgOD) | -0.00536 | 1.11 | 30.2 | 2.49 | 1 |
| □ Chimera 1 (MAP015-1/1: ng/ml vs AvgOD) | 0.0108 | 1.11 | 21.5 | 2.57 | 1 |

Curve Fit Option - Fixed Weight Value

```
                         SEQUENCE LISTING

<160> NUMBER OF SEQ ID NOS: 73

<210> SEQ ID NO 1
<211> LENGTH: 312
<212> TYPE: PRT
<213> ORGANISM: Homo sapiens
<220> FEATURE:
<221> NAME/KEY: PEPTIDE
<222> LOCATION: (1)...(312)
<223> OTHER INFORMATION: EMAPII Protein

<400> SEQUENCE: 1

Met Ala Asn Asn Asp Ala Val Leu Lys Arg Leu Glu Gln Lys Gly Ala
1               5                   10                  15

Glu Ala Asp Gln Ile Ile Glu Tyr Leu Lys Gln Gln Val Ser Leu Leu
            20                  25                  30

Lys Glu Lys Ala Ile Leu Gln Ala Thr Leu Arg Glu Glu Lys Lys Leu
        35                  40                  45

Arg Val Glu Asn Ala Lys Leu Lys Lys Glu Ile Glu Glu Leu Lys Gln
    50                  55                  60

Glu Leu Ile Gln Ala Glu Ile Gln Asn Gly Val Lys Gln Ile Pro Phe
65                  70                  75                  80

Pro Ser Gly Thr Pro Leu His Ala Asn Ser Met Val Ser Glu Asn Val
                85                  90                  95

Ile Gln Ser Thr Ala Val Thr Thr Val Ser Ser Gly Thr Lys Glu Gln
            100                 105                 110

Ile Lys Gly Gly Thr Gly Asp Glu Lys Lys Ala Lys Glu Lys Ile Glu
        115                 120                 125

Lys Lys Gly Glu Lys Lys Glu Lys Lys Gln Gln Ser Ile Ala Gly Ser
    130                 135                 140

Ala Asp Ser Lys Pro Ile Asp Val Ser Arg Leu Asp Leu Arg Ile Gly
145                 150                 155                 160

Cys Ile Ile Thr Ala Arg Lys His Pro Asp Ala Asp Ser Leu Tyr Val
                165                 170                 175

Glu Glu Val Asp Val Gly Glu Ile Ala Pro Arg Thr Val Val Ser Gly
            180                 185                 190

Leu Val Asn His Val Pro Leu Glu Gln Met Gln Asn Arg Met Val Ile
        195                 200                 205

Leu Leu Cys Asn Leu Lys Pro Ala Lys Met Arg Gly Val Leu Ser Gln
    210                 215                 220

Ala Met Val Met Cys Ala Ser Ser Pro Glu Lys Ile Glu Ile Leu Ala
225                 230                 235                 240

Pro Pro Asn Gly Ser Val Pro Gly Asp Arg Ile Thr Phe Asp Ala Phe
                245                 250                 255

Pro Gly Glu Pro Asp Lys Glu Leu Asn Pro Lys Lys Lys Ile Trp Glu
            260                 265                 270

Gln Ile Gln Pro Asp Leu His Thr Asn Asp Glu Cys Val Ala Thr Tyr
        275                 280                 285

Lys Gly Val Pro Phe Glu Val Lys Gly Lys Gly Val Cys Arg Ala Gln
    290                 295                 300

Thr Met Ser Asn Ser Gly Ile Lys
305                 310
```

<210> SEQ ID NO 2
<211> LENGTH: 30
<212> TYPE: DNA
<213> ORGANISM: Artificial Sequence
<220> FEATURE:
<223> OTHER INFORMATION: Forward primer for EMAPII

<400> SEQUENCE: 2
gcgaattcat ggcaaataat gatgctgttc          30

<210> SEQ ID NO 3
<211> LENGTH: 34
<212> TYPE: DNA
<213> ORGANISM: Artificial Sequence
<220> FEATURE:
<223> OTHER INFORMATION: Reverse primer for EMAPII

<400> SEQUENCE: 3
ccgctcgagt tatttgattc cactgttgct catg          34

<210> SEQ ID NO 4
<211> LENGTH: 16
<212> TYPE: DNA
<213> ORGANISM: Artificial Sequence
<220> FEATURE:
<223> OTHER INFORMATION: M13 Forward primer

<400> SEQUENCE: 4
gtaaaacgac ggccag          16

<210> SEQ ID NO 5
<211> LENGTH: 107
<212> TYPE: PRT
<213> ORGANISM: Artificial Sequence
<220> FEATURE:
<223> OTHER INFORMATION: Monoclonal Ab LC variable domain sequence

<400> SEQUENCE: 5

Asp Ile Val Met Thr Gln Ser His Lys Phe Met Ser Thr Ser Val Gly
 1               5                  10                  15

Asp Arg Val Ser Ile Thr Cys Lys Ala Ser Gln Asp Val Ser Thr Ala
                20                  25                  30

Val Ala Trp Tyr Gln Gln Lys Pro Gly Gln Ser Pro Lys Leu Leu Ile
            35                  40                  45

Phe Ser Ala Ser Tyr Arg Tyr Thr Gly Val Pro Asp Arg Phe Thr Gly
        50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Tyr
                85                  90                  95

Thr Phe Gly Gly Gly Thr Lys Leu Glu Ile Lys
                100                 105

<210> SEQ ID NO 6
<211> LENGTH: 120
<212> TYPE: PRT
<213> ORGANISM: Artificial Sequence
<220> FEATURE:
<223> OTHER INFORMATION: monoclonal Ab HC variable domain sequence

<400> SEQUENCE: 6

Gln Val Gln Leu Gln Gln Ser Gly Ala Glu Leu Ala Arg Pro Gly Ala
 1               5                  10                  15

```
Ser Val Lys Met Ser Cys Lys Ala Ser Gly Tyr Thr Phe Thr Ser Tyr
         20                  25                  30

Thr Met His Trp Val Lys Gln Arg Pro Gly Gln Gly Leu Glu Trp Ile
         35                  40                  45

Gly Tyr Ile Asn Pro Ser Ser Gly Phe Thr Asn Tyr Asn Gln Lys Phe
50                   55                  60

Lys Asp Lys Ala Thr Leu Thr Ala Asp Lys Ser Ser Ser Thr Ala Tyr
65                   70                  75                  80

Met Gln Leu Ser Ser Leu Thr Ser Glu Asp Ser Ala Val Tyr Tyr Cys
                 85                  90                  95

Ala Ser Arg Phe Ala Tyr Trp Gly Gln Gly Thr Leu Val Thr Val Ser
            100                 105                 110

Ala Ala Lys Thr Thr Pro Pro Ser
            115             120

<210> SEQ ID NO 7
<211> LENGTH: 25
<212> TYPE: DNA
<213> ORGANISM: Artificial Sequence
<220> FEATURE:
<223> OTHER INFORMATION: LC primer sequence (mVk19-17_leadF)

<400> SEQUENCE: 7
atggagtcac agattcaggt ctttg                                        25

<210> SEQ ID NO 8
<211> LENGTH: 26
<212> TYPE: DNA
<213> ORGANISM: Artificial Sequence
<220> FEATURE:
<223> OTHER INFORMATION: LC primer sequence (BAP015_LC_CDR3_R)

<400> SEQUENCE: 8
ccgaacgtgt acggagtact ataatg                                       26

<210> SEQ ID NO 9
<211> LENGTH: 18
<212> TYPE: DNA
<213> ORGANISM: Artificial Sequence
<220> FEATURE:
<223> OTHER INFORMATION: HC primer sequecne (mVHJ558_F)

<400> SEQUENCE: 9
caggtccagc tgcagcag                                                18

<210> SEQ ID NO 10
<211> LENGTH: 22
<212> TYPE: DNA
<213> ORGANISM: Artificial Sequence
<220> FEATURE:
<223> OTHER INFORMATION: HC primer sequence (BAP015_HV_CDR3_R)

<400> SEQUENCE: 10
ccccagtaag caaaccgact tg                                           22

<210> SEQ ID NO 11
<211> LENGTH: 101
<212> TYPE: PRT
<213> ORGANISM: Artificial Sequence
<220> FEATURE:
<223> OTHER INFORMATION: chimeric Ab LC variable domain

<400> SEQUENCE: 11
```

```
Asp Ile Val Met Thr Gln Ser His Lys Phe Met Ser Thr Ser Val Gly
 1               5                  10                  15

Asp Arg Val Ser Ile Thr Cys Lys Ala Ser Gln Asp Val Ser Thr Ala
                20                  25                  30

Val Ala Trp Tyr Gln Gln Lys Pro Gly Gln Ser Pro Lys Leu Leu Ile
            35                  40                  45

Phe Ser Ala Ser Tyr Arg Tyr Thr Gly Val Pro Asp Arg Phe Thr Gly
50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Tyr
                85                  90                  95

Thr Phe Gly Gln Gly
            100

<210> SEQ ID NO 12
<211> LENGTH: 101
<212> TYPE: PRT
<213> ORGANISM: Artificial Sequence
<220> FEATURE:
<223> OTHER INFORMATION: Humanized Ab LC variable domain_01

<400> SEQUENCE: 12

Ala Ile Gln Leu Thr Gln Ser Pro Ser Ser Leu Ser Ala Ser Val Gly
 1               5                  10                  15

Asp Arg Val Thr Ile Thr Cys Lys Ala Ser Gln Asp Val Ser Thr Ala
                20                  25                  30

Val Ala Trp Tyr Gln Gln Lys Pro Gly Gln Ala Pro Arg Leu Leu Ile
            35                  40                  45

Tyr Ser Ala Ser Tyr Arg Tyr Thr Gly Val Pro Ser Arg Phe Ser Gly
50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Gln His Tyr Ser Thr Pro Tyr
                85                  90                  95

Thr Phe Gly Gln Gly
            100

<210> SEQ ID NO 13
<211> LENGTH: 101
<212> TYPE: PRT
<213> ORGANISM: Artificial Sequence
<220> FEATURE:
<223> OTHER INFORMATION: Humanized Ab LC variable domain_02

<400> SEQUENCE: 13

Ala Ile Gln Leu Thr Gln Ser Pro Ser Ser Leu Ser Ala Ser Val Gly
 1               5                  10                  15

Asp Arg Val Thr Ile Thr Cys Lys Ala Ser Gln Asp Val Ser Thr Ala
                20                  25                  30

Val Ala Trp Tyr Gln Gln Lys Pro Gly Lys Ala Pro Lys Leu Leu Ile
            35                  40                  45

Tyr Ser Ala Ser Tyr Arg Tyr Thr Gly Ile Pro Pro Arg Phe Ser Gly
50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Gln Gln His Tyr Ser Thr Pro Tyr
```

85                  90                  95

Thr Phe Gly Gln Gly
            100

<210> SEQ ID NO 14
<211> LENGTH: 101
<212> TYPE: PRT
<213> ORGANISM: Artificial Sequence
<220> FEATURE:
<223> OTHER INFORMATION: Humanized Ab LC variable domain_03

<400> SEQUENCE: 14

Ala Ile Gln Leu Thr Gln Ser Pro Ser Ser Leu Ser Ala Ser Val Gly
  1               5                  10                  15

Asp Arg Val Thr Ile Thr Cys Lys Ala Ser Gln Asp Val Ser Thr Ala
                 20                  25                  30

Val Ala Trp Tyr Gln Gln Lys Pro Gly Lys Ala Pro Lys Leu Leu Ile
             35                  40                  45

Tyr Ser Ala Ser Tyr Arg Tyr Thr Gly Val Pro Ser Arg Phe Ser Gly
 50                  55                  60

Ser Gly Ser Gly Thr Asp Phe Thr Phe Thr Ile Ser Arg Leu Glu Pro
 65                  70                  75                  80

Glu Asp Phe Ala Val Tyr Tyr Cys Gln Gln His Tyr Ser Ile Pro Tyr
                 85                  90                  95

Thr Phe Gly Gln Gly
            100

<210> SEQ ID NO 15
<211> LENGTH: 101
<212> TYPE: PRT
<213> ORGANISM: Artificial Sequence
<220> FEATURE:
<223> OTHER INFORMATION: Humanized Ab LC variable domain_04

<400> SEQUENCE: 15

Ala Ile Gln Leu Thr Gln Ser Pro Ser Ser Leu Ser Ala Ser Val Gly
  1               5                  10                  15

Asp Arg Val Thr Ile Thr Cys Lys Ala Ser Gln Asp Val Ser Thr Ala
                 20                  25                  30

Val Ala Trp Tyr Gln Gln Lys Pro Gly Lys Ala Pro Lys Leu Leu Ile
             35                  40                  45

Tyr Ser Ala Ser Tyr Arg Tyr Thr Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln His Tyr Ser Thr Pro Tyr
                 85                  90                  95

Thr Phe Gly Gln Gly
            100

<210> SEQ ID NO 16
<211> LENGTH: 101
<212> TYPE: PRT
<213> ORGANISM: Artificial Sequence
<220> FEATURE:
<223> OTHER INFORMATION: Humanized Ab LC variable domain_05

<400> SEQUENCE: 16

Asp Ile Val Met Thr Gln Thr Pro Leu Ser Leu Pro Val Thr Pro Gly
  1               5                  10                  15

```
Glu Pro Ala Ser Ile Ser Cys Lys Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Ser Thr Pro Tyr
                85                  90                  95

Thr Phe Gly Gln Gly
            100

<210> SEQ ID NO 17
<211> LENGTH: 101
<212> TYPE: PRT
<213> ORGANISM: Artificial Sequence
<220> FEATURE:
<223> OTHER INFORMATION: Humanized Ab LC variable domain_06

<400> SEQUENCE: 17

Glu Ile Val Leu Thr Gln Ser Pro Asp Phe Gln Ser Val Thr Pro Lys
1               5                   10                  15

Glu Lys Val Thr Ile Thr Cys Lys Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Ser Thr Pro Tyr
                85                  90                  95

Thr Phe Gly Gln Gly
            100

<210> SEQ ID NO 18
<211> LENGTH: 101
<212> TYPE: PRT
<213> ORGANISM: Artificial Sequence
<220> FEATURE:
<223> OTHER INFORMATION: Humanized Ab LC variable domain_07

<400> SEQUENCE: 18

Glu Ile Val Leu Thr Gln Ser Pro Asp Phe Gln Ser Val Thr Pro Lys
1               5                   10                  15

Glu Lys Val Thr Ile Thr Cys Lys Ala Ser Gln Asp Val Ser Thr Ala
            20                  25                  30

Val Ala Trp Tyr Leu Gln Lys Pro Gly Gln Ser Pro Gln Leu Leu Ile
        35                  40                  45

Tyr Ser Ala Ser Tyr Arg Tyr Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Ser Thr Pro Tyr
                85                  90                  95

Thr Phe Gly Gln Gly
```

-continued

```
                100

<210> SEQ ID NO 19
<211> LENGTH: 106
<212> TYPE: PRT
<213> ORGANISM: Artificial Sequence
<220> FEATURE:
<223> OTHER INFORMATION: chimeric Ab HC variable domain

<400> SEQUENCE: 19

Gln Val Gln Leu Gln Gln Ser Gly Ala Glu Leu Ala Arg Pro Gly Ala
 1               5                  10                  15

Ser Val Lys Met Ser Cys Lys Ala Ser Gly Tyr Thr Phe Thr Ser Tyr
            20                  25                  30

Thr Met His Trp Val Lys Gln Arg Pro Gly Gln Gly Leu Glu Trp Ile
        35                  40                  45

Gly Tyr Ile Asn Pro Ser Ser Gly Phe Thr Asn Tyr Asn Gln Lys Phe
    50                  55                  60

Lys Asp Lys Ala Thr Leu Thr Ala Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Ser Arg Phe Ala Tyr Trp Gly Gln Gly
            100                 105

<210> SEQ ID NO 20
<211> LENGTH: 106
<212> TYPE: PRT
<213> ORGANISM: Artificial Sequence
<220> FEATURE:
<223> OTHER INFORMATION: humanized Ab HC variable domain_01

<400> SEQUENCE: 20

Glu Val Gln Leu Val Gln Ser Gly Ala Glu Val Lys Lys Pro Gly Glu
 1               5                  10                  15

Ser Leu Arg Ile Ser Cys Lys Gly Ser Gly Tyr Thr Phe Thr Ser Tyr
            20                  25                  30

Thr Met His Trp Ile Arg Gln Ser Pro Ser Arg Gly Leu Glu Trp Leu
        35                  40                  45

Gly Tyr Ile Asn Pro Ser Ser Gly Phe Thr Asn Tyr Asn Gln Lys Phe
    50                  55                  60

Lys Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Arg Phe Ala Tyr Trp Gly Gln Gly
            100                 105

<210> SEQ ID NO 21
<211> LENGTH: 106
<212> TYPE: PRT
<213> ORGANISM: Artificial Sequence
<220> FEATURE:
<223> OTHER INFORMATION: humanized Ab HC variable domain_02

<400> SEQUENCE: 21

Glu Val Gln Leu Val Gln Ser Gly Ala Glu Val Lys Lys Pro Gly Ala
 1               5                  10                  15

Thr Val Lys Ile Ser Cys Lys Val Ser Gly Tyr Thr Phe Thr Ser Tyr
            20                  25                  30
```

-continued

Thr Met His Trp Val Arg Gln Ala Pro Gly Gln Gly Leu Glu Trp Met
         35                  40                  45

Gly Tyr Ile Asn Pro Ser Ser Gly Phe Thr Asn Tyr Asn Gln Lys Phe
     50                  55                  60

Lys Asp Arg Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                 85                  90                  95

Ala Ser Arg Phe Ala Tyr Trp Gly Gln Gly
            100                 105

<210> SEQ ID NO 22
<211> LENGTH: 106
<212> TYPE: PRT
<213> ORGANISM: Artificial Sequence
<220> FEATURE:
<223> OTHER INFORMATION: Humanized Ab HC variable domain_03

<400> SEQUENCE: 22

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Ser Tyr
             20                  25                  30

Thr Met His Trp Val Arg Gln Ala Pro Gly Gln Gly Leu Glu Trp Met
         35                  40                  45

Gly Tyr Ile Asn Pro Ser Ser Gly Phe Thr Asn Tyr Asn Gln Lys Phe
     50                  55                  60

Lys Asp Arg Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                 85                  90                  95

Ala Ser Arg Phe Ala Tyr Trp Gly Gln Gly
            100                 105

<210> SEQ ID NO 23
<211> LENGTH: 106
<212> TYPE: PRT
<213> ORGANISM: Artificial Sequence
<220> FEATURE:
<223> OTHER INFORMATION: humanized Ab HC variable domain_04

<400> SEQUENCE: 23

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Ser Tyr
             20                  25                  30

Thr Met His Trp Val Arg Gln Ala Pro Gly Gln Gly Leu Glu Trp Met
         35                  40                  45

Gly Tyr Ile Asn Pro Ser Ser Gly Phe Thr Asn Tyr Asn Gln Lys Phe
     50                  55                  60

Lys Asp Arg Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                 85                  90                  95

Ala Ser Arg Phe Ala Tyr Trp Gly Gln Gly
            100                 105

-continued

```
<210> SEQ ID NO 24
<211> LENGTH: 106
<212> TYPE: PRT
<213> ORGANISM: Artificial Sequence
<220> FEATURE:
<223> OTHER INFORMATION: humanized Ab HC variable domain_05

<400> SEQUENCE: 24

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Ser Tyr
            20                  25                  30

Thr Met His Trp Val Arg Gln Ala Pro Gly Gln Gly Leu Glu Trp Met
        35                  40                  45

Gly Tyr Ile Asn Pro Ser Ser Gly Phe Thr Asn Tyr Asn Gln Lys Phe
    50                  55                  60

Lys Asp Arg Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Ser Arg Phe Ala Tyr Trp Gly Gln Gly
            100                 105

<210> SEQ ID NO 25
<211> LENGTH: 106
<212> TYPE: PRT
<213> ORGANISM: Artificial Sequence
<220> FEATURE:
<223> OTHER INFORMATION: humanized Ab HC variable domain_06

<400> SEQUENCE: 25

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Ser Tyr
            20                  25                  30

Thr Met His Trp Val Arg Gln Ala Pro Gly Gln Gly Leu Glu Trp Met
        35                  40                  45

Gly Tyr Ile Asn Pro Ser Ser Gly Phe Thr Asn Tyr Asn Gln Lys Phe
    50                  55                  60

Lys Asp Arg Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Ser Arg Phe Ala Tyr Trp Gly Gln Gly
            100                 105

<210> SEQ ID NO 26
<211> LENGTH: 106
<212> TYPE: PRT
<213> ORGANISM: Artificial Sequence
<220> FEATURE:
<223> OTHER INFORMATION: humanized Ab HC variable domain_07

<400> SEQUENCE: 26

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Ser Tyr
            20                  25                  30

Thr Met His Trp Val Arg Gln Ala Pro Gly Gln Gly Leu Glu Trp Met
        35                  40                  45
```

```
Gly Tyr Ile Asn Pro Ser Ser Gly Phe Thr Asn Tyr Asn Gln Lys Phe
            50                  55                  60

Lys Asp Arg Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                85                  90                  95

Ala Ser Arg Phe Ala Tyr Trp Gly Gln Gly
                100                 105

<210> SEQ ID NO 27
<211> LENGTH: 108
<212> TYPE: PRT
<213> ORGANISM: Mus musculus
<220> FEATURE:
<223> OTHER INFORMATION: Ig kappa-chain V-J2-C-region
<300> PUBLICATION INFORMATION:
<308> DATABASE ACCESSION NUMBER: GenBank: AAA39004.1
<309> DATABASE ENTRY DATE: 1993-06-12

<400> SEQUENCE: 27

Asp Ile Val Leu Thr Gln Ser Pro Ala Ser Leu Ala Val Ser Leu Gly
  1               5                  10                  15

Gln Arg Ala Thr Ile Ser Tyr Arg Ala Ser Lys Ser Val Ser Thr Ser
                 20                  25                  30

Gly Tyr Ser Tyr Met His Trp Asn Gln Gln Lys Pro Gly Gln Pro Pro
                35                  40                  45

Arg Leu Leu Ile Tyr Leu Val Ser Asn Leu Glu Ser Gly Val Pro Ala
             50                  55                  60

Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Gln His Ile Arg
                85                  90                  95

Glu Leu Thr Arg Ser Glu Gly Gly Pro Ser Trp Lys
                100                 105

<210> SEQ ID NO 28
<211> LENGTH: 95
<212> TYPE: PRT
<213> ORGANISM: Mus musculus
<220> FEATURE:
<223> OTHER INFORMATION: immunoglobulin kappa-chain mVk19-17

<400> SEQUENCE: 28

Asp Ile Val Met Thr Gln Ser His Lys Phe Met Ser Thr Ser Val Gly
  1               5                  10                  15

Asp Arg Val Ser Ile Thr Cys Lys Ala Ser Gln Asp Val Ser Thr Ala
                 20                  25                  30

Val Ala Trp Tyr Gln Gln Lys Pro Gly Gln Ser Pro Lys Leu Leu Ile
                35                  40                  45

Tyr Ser Ala Ser Tyr Arg Tyr Thr Gly Val Pro Asp Arg Phe Thr Gly
             50                  55                  60

Ser Gly Ser Gly Thr Asp Phe Thr Phe Thr Ile Ser Ser Val Gln Ala
 65                  70                  75                  80

Glu Asp Leu Ala Val Tyr Tyr Cys Gln Gln His Tyr Ser Thr Pro
                85                  90                  95

<210> SEQ ID NO 29
<211> LENGTH: 98
<212> TYPE: PRT
```

<213> ORGANISM: Mus musculus
<220> FEATURE:
<223> OTHER INFORMATION: immunoglobulin heavy chain mVh14-3*2

<400> SEQUENCE: 29

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Met His Trp Val Lys Gln Arg Pro Glu Gln Gly Leu Glu Trp Ile
        35                  40                  45

Gly Arg Ile Asp Pro Ala Asn Gly Asn Thr Lys Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg

<210> SEQ ID NO 30
<211> LENGTH: 98
<212> TYPE: PRT
<213> ORGANISM: Mus musculus
<220> FEATURE:
<223> OTHER INFORMATION: immunoglobulin heavy chain mVh1-4*1

<400> SEQUENCE: 30

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Ser Tyr
            20                  25                  30

Thr Met His Trp Val Lys Gln Arg Pro Gly Gln Gly Leu Glu Trp Ile
        35                  40                  45

Gly Tyr Ile Asn Pro Ser Ser Gly Tyr Thr Lys Tyr Asn Gln Lys Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg

<210> SEQ ID NO 31
<211> LENGTH: 321
<212> TYPE: DNA
<213> ORGANISM: Artificial Sequence
<220> FEATURE:
<223> OTHER INFORMATION: Forward sequence for monoclonal Ab LC variable
      domain

<400> SEQUENCE: 31
gacattgtga tgacccagtc tcacaaattc atgtccacat cagtaggaga cagggtcagc      60
atcacctgca aggccagtca ggatgtgast actgctgtag cctggtatca acagaaacca     120
ggacaatctc ctaaactact gattttctcg gcatcctacc ggtacactgg agtccctgat     180
cgcttcactg gcagtggatc tgggacggat ttcactttca ccatcagcag tgtgcaggct     240
gaagacctgg cagtttatta ctgtcagcaa cattatagta ctccgtacac gttcggaggg     300
gggaccaagc tggaaataaa a                                              321

<210> SEQ ID NO 32
<211> LENGTH: 321
<212> TYPE: DNA
<213> ORGANISM: Artificial Sequence
<220> FEATURE:
<223> OTHER INFORMATION: Reverse sequence for monoclonal Ab LC variable domain

<400> SEQUENCE: 32

```
ttttatttcc agcttggtcc cccctccgaa cgtgtacgga gtactataat gttgctgaca      60
gtaataaact gccaggtctt cagcctgcac actgctgatg gtgaaagtga atccgtccc     120 agatccactg ccagtgaagc gatcaggggac tccagtgtac cggtaggatg ccagaaaat    180 cagtagttta ggagattgtc ctggtttctg ttgataccag gctacagcag tactcacatc    240
ctgactggcc ttgcaggtga tgctgaccct gtctcctact gatgtggaca tgaatttgtg    300
agactgggtc atcacaatgt c                                               321
```

<210> SEQ ID NO 33
<211> LENGTH: 360
<212> TYPE: DNA
<213> ORGANISM: Artificial Sequence
<220> FEATURE:
<223> OTHER INFORMATION: Forward sequence for monoclonal Ab HC variable domain

<400> SEQUENCE: 33

```
caggtccagc tgcagcagtc tggggctgaa ctggcaagac ctggggcctc agtgaagatg      60
tcctgcaagg cttctggcta cacctttact agctacacga tgcactgggt aaaacagagg    120
cctggacagg gtctggaatg gattggatac attaatccta gcagtggttt tactaattac    180
aatcagaagt tcaaggacaa ggccacattg actgcagaca atcctccag cacagcctac     240 atgcaactga gcagcctgac atctgaggac tctgcagtct attactgtgc aagtcggttt    300
gcttactggg gccaagggac tctggtcact gtctctgcag ccaaaacgac ccccccatct    360
```

<210> SEQ ID NO 34
<211> LENGTH: 360
<212> TYPE: DNA
<213> ORGANISM: Artificial Sequence
<220> FEATURE:
<223> OTHER INFORMATION: Reverse sequence for monoclonal Ab HC variable domain

<400> SEQUENCE: 34

```
agatggggggt gtcgttttgg ctgcagagac agtgaccaga gtcccttggc cccagtaagc     60
aaaccgactt gcacagtaat agactgcaga gtcctcagat gtcaggctgc tcagttgcat    120
gtaggctgtg ctgaggatt tgtctgcagt caatgtggcc ttgtccttga acttctgatt    180
gtaattagta aaaccactgc taggattaat gtatccaatc cattccagac cctgtccagg    240
cctctgtttt acccagtgca tcgtgtagct agtaaaggtg tagccagaag ccttgcagga    300
catcttcact gaggccccag gtcttgccag ttcagcccca gactgctgca gctggacctg    360
```

<210> SEQ ID NO 35
<211> LENGTH: 108
<212> TYPE: PRT
<213> ORGANISM: Artificial Sequence
<220> FEATURE:
<223> OTHER INFORMATION: light chain sequence K2-1-T7

<400> SEQUENCE: 35

```
Asn Ile Val Leu Thr Gln Ser Pro Ala Ser Leu Ala Val Ser Leu Gly
 1               5                  10                  15

Gln Arg Ala Thr Ile Ser Tyr Arg Ala Ser Lys Ser Val Ser Thr Ser
            20                  25                  30

Gly Tyr Ser Tyr Met His Trp Asn Gln Gln Lys Pro Gly Gln Pro Pro
        35                  40                  45

Arg Leu Leu Ile Tyr Leu Val Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ile Arg
                85                  90                  95

Glu Leu Thr Arg Ser Glu Gly Gly Pro Ser Trp Lys
            100                 105
```

<210> SEQ ID NO 36
<211> LENGTH: 108
<212> TYPE: PRT
<213> ORGANISM: Artificial Sequence
<220> FEATURE:
<223> OTHER INFORMATION: light chain sequence K2-2-T7

<400> SEQUENCE: 36

```
Asp Ile Val Leu Thr Gln Ser Pro Ala Ser Leu Ala Val Ser Leu Gly
 1               5                  10                  15

Gln Arg Ala Thr Ile Ser Tyr Arg Ala Ser Lys Ser Val Ser Thr Ser
            20                  25                  30

Gly Tyr Ser Tyr Met His Trp Asn Gln Gln Lys Pro Gly Gln Pro Pro
        35                  40                  45

Arg Leu Leu Ile Tyr Leu Val Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ile Arg
                85                  90                  95

Glu Leu Thr Arg Ser Glu Gly Gly Pro Ser Trp Lys
            100                 105
```

<210> SEQ ID NO 37
<211> LENGTH: 107
<212> TYPE: PRT
<213> ORGANISM: Artificial Sequence
<220> FEATURE:
<223> OTHER INFORMATION: light chain sequence K2-3-T7

<400> SEQUENCE: 37

```
Ile Val Leu Thr Gln Ser Pro Ala Ser Leu Ala Val Ser Leu Gly Gln
 1               5                  10                  15

Arg Ala Thr Ile Ser Tyr Arg Ala Ser Lys Ser Val Ser Thr Ser Gly
            20                  25                  30

Tyr Ser Tyr Met His Trp Asn Gln Gln Lys Pro Gly Gln Pro Pro Arg
        35                  40                  45

Leu Leu Ile Tyr Leu Val Ser Asn Leu Glu Ser Gly Val Pro Ala Arg
    50                  55                  60

Phe Ser Gly Ser Gly Ser Gly Thr Asp Phe Thr Leu Asn Ile His Pro
65                  70                  75                  80

Val Glu Glu Glu Asp Ala Ala Thr Tyr Tyr Cys Gln His Ile Arg Glu
                85                  90                  95
```

```
Leu Thr Arg Ser Glu Gly Gly Pro Ser Trp Lys
            100                 105
```

<210> SEQ ID NO 38
<211> LENGTH: 107
<212> TYPE: PRT
<213> ORGANISM: Artificial Sequence
<220> FEATURE:
<223> OTHER INFORMATION: light chain sequence K2-4-T7

<400> SEQUENCE: 38

```
Ile Val Leu Thr Gln Ser Pro Ala Ser Leu Ala Val Ser Leu Gly Gln
 1               5                  10                  15

Arg Ala Thr Ile Ser Tyr Arg Ala Ser Lys Ser Val Ser Thr Ser Gly
            20                  25                  30

Tyr Ser Tyr Met His Trp Asn Gln Gln Lys Pro Gly Gln Pro Pro Arg
        35                  40                  45

Leu Leu Ile Tyr Leu Val Ser Asn Leu Glu Ser Gly Val Pro Ala Arg
    50                  55                  60

Phe Ser Gly Ser Gly Ser Gly Thr Asp Phe Thr Leu Asn Ile His Pro
65                  70                  75                  80

Val Glu Glu Asp Ala Ala Thr Tyr Tyr Cys Gln His Ile Arg Glu
                85                  90                  95

Leu Thr Arg Ser Glu Gly Gly Pro Ser Trp Lys
            100                 105
```

<210> SEQ ID NO 39
<211> LENGTH: 108
<212> TYPE: PRT
<213> ORGANISM: Artificial Sequence
<220> FEATURE:
<223> OTHER INFORMATION: light chain sequence K2-5-T7

<400> SEQUENCE: 39

```
Asp Ile Val Leu Thr Gln Ser Pro Ala Ser Leu Ala Val Ser Leu Gly
 1               5                  10                  15

Gln Arg Ala Thr Ile Ser Tyr Arg Ala Ser Lys Ser Val Ser Thr Ser
            20                  25                  30

Gly Tyr Ser Tyr Met His Trp Asn Gln Gln Lys Pro Gly Gln Pro Pro
        35                  40                  45

Arg Leu Leu Ile Tyr Leu Val Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Asp Ala Ala Thr Tyr Tyr Cys Gln His Ile Arg
                85                  90                  95

Glu Leu Thr Arg Ser Glu Gly Gly Pro Ser Trp Lys
            100                 105
```

<210> SEQ ID NO 40
<211> LENGTH: 108
<212> TYPE: PRT
<213> ORGANISM: Artificial Sequence
<220> FEATURE:
<223> OTHER INFORMATION: light chain sequence K2-6-T7

<400> SEQUENCE: 40

```
Asp Ile Val Leu Thr Gln Ser Pro Ala Ser Leu Ala Val Ser Leu Gly
 1               5                  10                  15
```

```
Gln Arg Ala Thr Ile Ser Tyr Arg Ala Ser Lys Ser Val Ser Thr Ser
            20                  25                  30

Gly Tyr Ser Tyr Met His Trp Asn Gln Gln Lys Pro Gly Gln Pro Pro
        35                  40                  45

Arg Leu Leu Ile Tyr Leu Val Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ile Arg
                85                  90                  95

Glu Leu Thr Arg Ser Glu Gly Gly Pro Ser Trp Glu
            100                 105
```

<210> SEQ ID NO 41
<211> LENGTH: 108
<212> TYPE: PRT
<213> ORGANISM: Artificial Sequence
<220> FEATURE:
<223> OTHER INFORMATION: light chain sequence K3-2-T7

<400> SEQUENCE: 41

```
Glu Asn Val Leu Thr Gln Ser Pro Ala Ser Leu Ala Val Ser Leu Gly
1               5                   10                  15

Gln Arg Ala Thr Ile Ser Tyr Arg Ala Ser Lys Ser Val Ser Thr Ser
            20                  25                  30

Gly Tyr Ser Tyr Met His Trp Asn Gln Gln Lys Pro Gly Gln Pro Pro
        35                  40                  45

Arg Leu Leu Ile Tyr Leu Val Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ile Arg
                85                  90                  95

Glu Leu Thr Arg Ser Glu Gly Gly Pro Ser Trp Lys
            100                 105
```

<210> SEQ ID NO 42
<211> LENGTH: 108
<212> TYPE: PRT
<213> ORGANISM: Artificial Sequence
<220> FEATURE:
<223> OTHER INFORMATION: light chain sequence K3-4-T7

<400> SEQUENCE: 42

```
Glu Asn Val Leu Ser Gln Ser Pro Ala Ser Leu Ala Val Ser Leu Gly
1               5                   10                  15

Gln Arg Ala Thr Ile Ser Tyr Arg Ala Ser Lys Ser Val Ser Thr Ser
            20                  25                  30

Gly Tyr Ser Tyr Met His Trp Asn Gln Gln Lys Pro Gly Gln Pro Pro
        35                  40                  45

Arg Leu Leu Ile Tyr Leu Val Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ile Arg
                85                  90                  95

Glu Leu Thr Arg Ser Glu Gly Gly Pro Ser Trp Lys
            100                 105
```

<210> SEQ ID NO 43
<211> LENGTH: 108
<212> TYPE: PRT
<213> ORGANISM: Artificial Sequence
<220> FEATURE:
<223> OTHER INFORMATION: light chain sequence K3-5-T7

<400> SEQUENCE: 43

```
Glu Asn Val Leu Thr Gln Ser Pro Ala Ser Leu Ala Val Ser Leu Gly
  1               5                  10                  15

Gln Arg Ala Thr Ile Ser Tyr Arg Ala Ser Lys Ser Val Ser Thr Ser
             20                  25                  30

Gly Tyr Ser Tyr Met His Trp Asn Gln Gln Lys Pro Gly Gln Pro Pro
         35                  40                  45

Arg Leu Leu Ile Tyr Leu Val Ser Asn Leu Glu Ser Gly Val Pro Ala
     50                  55                  60

Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Gln His Ile Arg
                 85                  90                  95

Glu Leu Thr Arg Ser Glu Gly Gly Pro Ser Trp Lys
            100                 105
```

<210> SEQ ID NO 44
<211> LENGTH: 108
<212> TYPE: PRT
<213> ORGANISM: Artificial Sequence
<220> FEATURE:
<223> OTHER INFORMATION: light chain sequence K3-6-T7

<400> SEQUENCE: 44

```
Glu Asn Val Leu Thr Gln Ser Pro Ala Ser Leu Ala Val Ser Leu Gly
  1               5                  10                  15

Gln Arg Ala Thr Ile Ser Tyr Arg Ala Ser Lys Ser Val Ser Thr Ser
             20                  25                  30

Gly Tyr Ser Tyr Met His Trp Asn Gln Gln Lys Pro Gly Gln Pro Pro
         35                  40                  45

Arg Leu Leu Ile Tyr Leu Val Ser Asn Leu Glu Ser Gly Val Pro Ala
     50                  55                  60

Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Gln His Ile Arg
                 85                  90                  95

Glu Leu Thr Arg Ser Glu Gly Gly Pro Ser Trp Lys
            100                 105
```

<210> SEQ ID NO 45
<211> LENGTH: 107
<212> TYPE: PRT
<213> ORGANISM: Artificial Sequence
<220> FEATURE:
<223> OTHER INFORMATION: light chain sequence K6-2

<400> SEQUENCE: 45

```
Ser Ile Val Met Thr Gln Thr His Lys Phe Met Ser Thr Ser Val Gly
  1               5                  10                  15

Asp Arg Val Ser Ile Thr Cys Lys Ala Ser Gln Asp Val Ser Thr Ala
             20                  25                  30
```

-continued

Val Ala Trp Tyr Gln Gln Lys Pro Gly Gln Ser Pro Lys Leu Leu Ile
             35                  40                  45

Phe Ser Ala Ser Tyr Arg Tyr Thr Gly Val Pro Asp Arg Phe Thr Gly
 50                  55                  60

Ser Gly Ser Gly Thr Asp Phe Thr Phe Thr Ile Ser Ser Val Gln Ala
 65                  70                  75                  80

Glu Asp Leu Ala Val Tyr Tyr Cys Gln Gln His Tyr Ser Thr Pro Tyr
                 85                  90                  95

Thr Phe Gly Gly Gly Thr Lys Leu Glu Ile Lys
                100                 105

<210> SEQ ID NO 46
<211> LENGTH: 107
<212> TYPE: PRT
<213> ORGANISM: Artificial Sequence
<220> FEATURE:
<223> OTHER INFORMATION: light chain sequence K6-1

<400> SEQUENCE: 46

Ser Ile Val Met Thr Gln Ser His Lys Phe Met Ser Thr Ser Val Gly
 1               5                  10                  15

Asp Arg Val Ser Ile Thr Cys Lys Ala Ser Gln Asp Val Ser Thr Ala
             20                  25                  30

Val Ala Trp Tyr Gln Gln Lys Pro Gly Gln Ser Pro Lys Leu Leu Ile
         35                  40                  45

Phe Ser Ala Ser Tyr Arg Tyr Thr Gly Val Pro Asp Arg Phe Thr Gly
 50                  55                  60

Ser Gly Ser Gly Thr Asp Phe Thr Phe Thr Ile Ser Ser Val Gln Ala
 65                  70                  75                  80

Glu Asp Leu Ala Val Tyr Tyr Cys Gln Gln His Tyr Ser Thr Pro Tyr
                 85                  90                  95

Thr Phe Gly Gly Gly Thr Lys Leu Glu Ile Lys
                100                 105

<210> SEQ ID NO 47
<211> LENGTH: 107
<212> TYPE: PRT
<213> ORGANISM: Artificial Sequence
<220> FEATURE:
<223> OTHER INFORMATION: light chain sequence K7-3

<400> SEQUENCE: 47

Ser Ile Val Met Thr Gln Ser Pro Lys Phe Met Ser Thr Ser Val Gly
 1               5                  10                  15

Asp Arg Val Ser Ile Thr Cys Lys Ala Ser Gln Asp Val Ser Thr Ala
             20                  25                  30

Val Ala Trp Tyr Gln Gln Lys Pro Gly Gln Ser Pro Lys Leu Leu Ile
         35                  40                  45

Phe Ser Ala Ser Tyr Arg Tyr Thr Gly Val Pro Asp Arg Phe Thr Gly
 50                  55                  60

Ser Gly Ser Gly Thr Asp Phe Thr Phe Thr Ile Ser Ser Val Gln Ala
 65                  70                  75                  80

Glu Asp Leu Ala Val Tyr Tyr Cys Gln Gln His Tyr Ser Thr Pro Tyr
                 85                  90                  95

Thr Phe Gly Gly Gly Thr Lys Leu Glu Ile Lys
                100                 105

<210> SEQ ID NO 48

```
<211> LENGTH: 107
<212> TYPE: PRT
<213> ORGANISM: Artificial Sequence
<220> FEATURE:
<223> OTHER INFORMATION: light chain sequence K7-6

<400> SEQUENCE: 48

Asn Ile Val Met Thr Gln Thr Pro Lys Phe Met Ser Thr Ser Val Gly
 1               5                  10                  15

Asp Arg Val Ser Ile Thr Cys Lys Ala Ser Gln Asp Val Ser Thr Ala
             20                  25                  30

Val Ala Trp Tyr Gln Gln Lys Pro Gly Gln Ser Pro Lys Leu Leu Ile
         35                  40                  45

Phe Ser Ala Ser Tyr Arg Tyr Thr Gly Val Pro Asp Arg Phe Thr Gly
     50                  55                  60

Ser Gly Ser Gly Thr Asp Phe Thr Phe Thr Ile Ser Ser Val Gln Ala
 65                  70                  75                  80

Glu Asp Leu Ala Val Tyr Tyr Cys Gln Gln His Tyr Ser Thr Pro Tyr
                 85                  90                  95

Thr Phe Gly Gly Gly Thr Lys Leu Glu Ile Lys
            100                 105

<210> SEQ ID NO 49
<211> LENGTH: 107
<212> TYPE: PRT
<213> ORGANISM: Artificial Sequence
<220> FEATURE:
<223> OTHER INFORMATION: light chain sequence K8-1

<400> SEQUENCE: 49

Gly Ile Val Met Thr Gln Ser His Lys Phe Met Ser Thr Ser Val Gly
 1               5                  10                  15

Asp Arg Val Ser Ile Thr Cys Lys Ala Ser Gln Asp Val Ser Thr Ala
             20                  25                  30

Val Ala Trp Tyr Gln Gln Lys Pro Gly Gln Ser Pro Lys Leu Leu Ile
         35                  40                  45

Phe Ser Ala Ser Tyr Arg Tyr Thr Gly Val Pro Asp Arg Phe Thr Gly
     50                  55                  60

Ser Gly Ser Gly Thr Asp Phe Thr Phe Thr Ile Ser Ser Val Gln Ala
 65                  70                  75                  80

Glu Asp Leu Ala Val Tyr Tyr Cys Gln Gln His Tyr Ser Thr Pro Tyr
                 85                  90                  95

Thr Phe Gly Gly Gly Thr Lys Leu Glu Ile Lys
            100                 105

<210> SEQ ID NO 50
<211> LENGTH: 107
<212> TYPE: PRT
<213> ORGANISM: Artificial Sequence
<220> FEATURE:
<223> OTHER INFORMATION: light chain sequence K8-2

<400> SEQUENCE: 50

Asp Ile Val Met Thr Gln Thr His Lys Phe Met Ser Thr Ser Val Gly
 1               5                  10                  15

Asp Arg Val Ser Ile Thr Cys Lys Ala Ser Gln Asp Val Ser Thr Ala
             20                  25                  30

Val Ala Trp Tyr Gln Gln Lys Pro Gly Gln Ser Pro Lys Leu Leu Ile
         35                  40                  45
```

```
Phe Ser Ala Ser Tyr Arg Tyr Thr Gly Val Pro Asp Arg Phe Thr Gly
         50                  55                  60

Ser Gly Ser Gly Thr Asp Phe Thr Phe Thr Ile Ser Ser Val Gln Ala
 65                  70                  75                  80

Glu Asp Leu Ala Val Tyr Tyr Cys Gln Gln His Tyr Ser Thr Pro Tyr
                 85                  90                  95

Thr Phe Gly Gly Gly Thr Lys Leu Glu Ile Lys
                100                 105

<210> SEQ ID NO 51
<211> LENGTH: 107
<212> TYPE: PRT
<213> ORGANISM: Artificial Sequence
<220> FEATURE:
<223> OTHER INFORMATION: light chain sequence K9-1

<400> SEQUENCE: 51

Gly Ile Val Met Thr Gln Thr Pro Lys Phe Met Ser Thr Ser Val Gly
 1               5                  10                  15

Asp Arg Val Ser Ile Thr Cys Lys Ala Ser Gln Asp Val Ser Thr Ala
                 20                  25                  30

Val Ala Trp Tyr Gln Gln Lys Pro Gly Gln Ser Pro Lys Leu Leu Ile
             35                  40                  45

Phe Ser Ala Ser Tyr Arg Tyr Thr Gly Val Pro Asp Arg Phe Thr Gly
         50                  55                  60

Ser Gly Ser Gly Thr Asp Phe Thr Phe Thr Ile Ser Ser Val Gln Ala
 65                  70                  75                  80

Glu Asp Leu Ala Val Tyr Tyr Cys Gln Gln His Tyr Ser Thr Pro Tyr
                 85                  90                  95

Thr Phe Gly Gly Gly Thr Lys Leu Glu Ile Lys
                100                 105

<210> SEQ ID NO 52
<211> LENGTH: 107
<212> TYPE: PRT
<213> ORGANISM: Artificial Sequence
<220> FEATURE:
<223> OTHER INFORMATION: light chain sequence K9-5

<400> SEQUENCE: 52

Asp Ile Val Met Thr Gln Thr Pro Lys Phe Met Ser Thr Ser Val Gly
 1               5                  10                  15

Asp Arg Val Ser Ile Thr Cys Lys Ala Ser Gln Asp Val Ser Thr Ala
                 20                  25                  30

Val Ala Trp Tyr Gln Gln Lys Pro Gly Gln Ser Pro Lys Leu Leu Ile
             35                  40                  45

Phe Ser Ala Ser Tyr Arg Tyr Thr Gly Val Pro Asp Arg Phe Thr Gly
         50                  55                  60

Ser Gly Ser Gly Thr Asp Phe Thr Phe Thr Ile Ser Ser Val Gln Ala
 65                  70                  75                  80

Glu Asp Leu Ala Val Tyr Tyr Cys Gln Gln His Tyr Ser Thr Pro Tyr
                 85                  90                  95

Thr Phe Gly Gly Gly Thr Lys Leu Glu Ile Lys
                100                 105

<210> SEQ ID NO 53
<211> LENGTH: 107
<212> TYPE: PRT
<213> ORGANISM: Artificial Sequence
```

<220> FEATURE:
<223> OTHER INFORMATION: light chain sequence K11-1

<400> SEQUENCE: 53

Asp Ile Met Met Thr Gln Ser Pro Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Phe Ser Ala Ser Tyr Arg Tyr Thr Gly Val Pro Asp Arg Phe Thr Gly
50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Tyr
                85                  90                  95

Thr Phe Gly Gly Gly Thr Lys Leu Glu Ile Lys
            100                 105

<210> SEQ ID NO 54
<211> LENGTH: 106
<212> TYPE: PRT
<213> ORGANISM: Artificial Sequence
<220> FEATURE:
<223> OTHER INFORMATION: light chain sequence K11-3

<400> SEQUENCE: 54

Glu Ile Lys Thr Gln Ser Pro Lys Phe Met Ser Thr Ser Val Gly Asp
1               5                   10                  15

Arg Val Ser Ile Thr Cys Lys Ala Ser Gln Asp Val Ser Thr Ala Val
            20                  25                  30

Ala Trp Tyr Gln Gln Lys Pro Gly Gln Ser Pro Lys Leu Leu Ile Phe
        35                  40                  45

Ser Ala Ser Tyr Arg Tyr Thr Gly Val Pro Asp Arg Phe Thr Gly Ser
50                  55                  60

Gly Ser Gly Thr Asp Phe Thr Phe Thr Ile Ser Ser Val Gln Ala Glu
65                  70                  75                  80

Asp Leu Ala Val Tyr Tyr Cys Gln Gln His Tyr Ser Thr Pro Tyr Thr
                85                  90                  95

Phe Gly Gly Gly Thr Lys Leu Glu Ile Lys
            100                 105

<210> SEQ ID NO 55
<211> LENGTH: 107
<212> TYPE: PRT
<213> ORGANISM: Artificial Sequence
<220> FEATURE:
<223> OTHER INFORMATION: light chain sequence K11-4

<400> SEQUENCE: 55

Glu Ile Met Met Thr Gln Ser Pro Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Phe Ser Ala Ser Tyr Arg Tyr Thr Gly Val Pro Asp Arg Phe Thr Gly
50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Tyr
                85                  90                  95

Thr Phe Gly Gly Gly Thr Lys Leu Glu Ile Lys
            100                 105

<210> SEQ ID NO 56
<211> LENGTH: 107
<212> TYPE: PRT
<213> ORGANISM: Artificial Sequence
<220> FEATURE:
<223> OTHER INFORMATION: light chain sequence K11-5

<400> SEQUENCE: 56

Asp Ile Lys Met Thr Gln Ser Pro Lys Phe Met Ser Thr Ser Val Gly
1               5                   10                  15

Asp Arg Val Ser Ile Thr Cys Lys Ala Ser Gln Asp Val Ser Thr Ala
                20                  25                  30

Val Ala Trp Tyr Gln Gln Lys Pro Gly Gln Ser Pro Lys Leu Leu Ile
            35                  40                  45

Phe Ser Ala Ser Tyr Arg Tyr Thr Gly Val Pro Asp Arg Phe Thr Gly
50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Tyr
                85                  90                  95

Thr Phe Gly Gly Gly Thr Lys Leu Glu Ile Lys
            100                 105

<210> SEQ ID NO 57
<211> LENGTH: 102
<212> TYPE: PRT
<213> ORGANISM: Artificial Sequence
<220> FEATURE:
<223> OTHER INFORMATION: heavy chain sequence H4-4

<400> SEQUENCE: 57

Glu Trp Met Leu Val Glu Ser Gly Ala Glu Leu Val Lys Pro Gly Ala
1               5                   10                  15

Ser Val Lys Leu Ser Cys Thr Ala Ser Gly Phe Asn Ile Lys Asp Thr
                20                  25                  30

Tyr Met His Trp Val Lys Gln Arg Pro Glu Gln Gly Leu Glu Trp Ile
            35                  40                  45

Gly Arg Ile Asp Pro Ala Asn Gly Asn Thr Lys Tyr Asp Pro Lys Phe
50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg Arg Gly Leu Leu
            100

<210> SEQ ID NO 58
<211> LENGTH: 102
<212> TYPE: PRT
<213> ORGANISM: Artificial Sequence
<220> FEATURE:
<223> OTHER INFORMATION: heavy chain sequence H4-5

```
<400> SEQUENCE: 58

Glu Val Met Leu Val Glu Ser Glu Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Met His Trp Val Lys Gln Arg Pro Glu Gln Gly Leu Glu Trp Ile
        35                  40                  45

Gly Arg Ile Asp Pro Ala Asn Gly Asn Thr Lys Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg Arg Gly Leu Leu
            100

<210> SEQ ID NO 59
<211> LENGTH: 102
<212> TYPE: PRT
<213> ORGANISM: Artificial Sequence
<220> FEATURE:
<223> OTHER INFORMATION: heavy chain sequence H4-6

<400> SEQUENCE: 59

Glu Val Met Leu Val Glu Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Met His Trp Val Lys Gln Arg Pro Glu Gln Gly Leu Glu Trp Ile
        35                  40                  45

Gly Arg Ile Asp Pro Ala Asn Gly Asn Thr Lys Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg Arg Gly Leu Leu
            100

<210> SEQ ID NO 60
<211> LENGTH: 121
<212> TYPE: PRT
<213> ORGANISM: Artificial Sequence
<220> FEATURE:
<223> OTHER INFORMATION: heavy chain sequence H1-1

<400> SEQUENCE: 60

Gln Val Gln Leu Gln Gln Pro Gly Ala Glu Leu Ala Arg Pro Gly Ala
1               5                   10                  15

Ser Val Lys Met Ser Cys Lys Ala Ser Gly Tyr Thr Phe Thr Ser Tyr
            20                  25                  30

Ala Met His Trp Val Lys Gln Arg Pro Gly Gln Gly Leu Glu Trp Ile
        35                  40                  45

Gly Tyr Ile Asn Pro Ser Ser Gly Phe Thr Asn Tyr Asn Gln Lys Phe
    50                  55                  60

Lys Asp Lys Ala Thr Leu Thr Ala Asp Lys Ser Ser Ser Thr Ala Tyr
65                  70                  75                  80
```

```
Met Gln Leu Ser Ser Leu Thr Ser Glu Asp Ser Ala Val Tyr Tyr Cys
                85                  90                  95

Ala Arg Ser Arg Phe Ala Tyr Trp Gly Gln Gly Thr Leu Val Thr Val
            100                 105                 110

Ser Ala Ala Lys Thr Thr Pro Pro Ser
            115                 120

<210> SEQ ID NO 61
<211> LENGTH: 121
<212> TYPE: PRT
<213> ORGANISM: Artificial Sequence
<220> FEATURE:
<223> OTHER INFORMATION: heavy chain sequence H1-2

<400> SEQUENCE: 61

Ala Val Gln Leu Gln Gln Phe Gly Ala Glu Leu Ala Arg Pro Gly Ala
1               5                   10                  15

Ser Val Lys Met Ser Cys Lys Ala Ser Gly Tyr Thr Phe Thr Ser Tyr
            20                  25                  30

Thr Met His Trp Val Lys Gln Arg Pro Gly Gln Gly Leu Glu Trp Ile
            35                  40                  45

Gly Tyr Ile Asn Pro Ser Ser Gly Phe Thr Asn Tyr Asn Gln Lys Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Arg Phe Ala Tyr Trp Gly Gln Gly Thr Leu Val Thr Val
            100                 105                 110

Ser Ala Ala Lys Thr Thr Pro Pro Ser
            115                 120

<210> SEQ ID NO 62
<211> LENGTH: 121
<212> TYPE: PRT
<213> ORGANISM: Artificial Sequence
<220> FEATURE:
<223> OTHER INFORMATION: heavy chain sequence H1-3

<400> SEQUENCE: 62

Glu Val Gln Leu Gln Gln Leu Gly Ala Glu Leu Ala Arg Pro Gly Ala
1               5                   10                  15

Ser Val Lys Met Ser Cys Lys Ala Ser Gly Tyr Thr Phe Thr Ser Tyr
            20                  25                  30

Thr Met His Trp Val Lys Gln Arg Pro Gly Gln Gly Leu Glu Trp Ile
            35                  40                  45

Gly Tyr Ile Asn Pro Ser Ser Gly Phe Thr Asn Tyr Asn Gln Lys Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Pro Glu Asp Ser Ala Val Tyr Tyr Cys
                85                  90                  95

Ala Arg Ser Arg Phe Ala Tyr Trp Gly Gln Gly Thr Leu Val Thr Val
            100                 105                 110

Ser Ala Ala Lys Thr Thr Pro Pro Ser
            115                 120

<210> SEQ ID NO 63
```

<211> LENGTH: 121
<212> TYPE: PRT
<213> ORGANISM: Artificial Sequence
<220> FEATURE:
<223> OTHER INFORMATION: heavy chain sequence H2-4

<400> SEQUENCE: 63

Pro Val Gln Leu Lys Glu Ser Gly Ala Glu Leu Ala Arg Pro Gly Ala
1               5                   10                  15

Ser Val Lys Met Ser Cys Lys Ala Ser Gly Tyr Thr Phe Thr Ser Tyr
            20                  25                  30

Thr Met His Trp Val Lys Gln Arg Pro Gly Gln Gly Leu Glu Trp Ile
        35                  40                  45

Gly Tyr Ile Asn Pro Ser Ser Gly Phe Thr Asn Tyr Asn Gln Lys Phe
    50                  55                  60

Lys Asp Lys Ala Thr Leu Thr Ala Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Arg Phe Ala Tyr Trp Gly Gln Gly Thr Leu Val Thr Val
            100                 105                 110

Ser Ala Ala Lys Thr Thr Pro Pro Ser
        115                 120

<210> SEQ ID NO 64
<211> LENGTH: 118
<212> TYPE: PRT
<213> ORGANISM: Artificial Sequence
<220> FEATURE:
<223> OTHER INFORMATION: heavy chain sequence H3-1

<400> SEQUENCE: 64

Leu Gln Gln Ser Gly Ala Glu Leu Ala Arg Phe Gly Ala Ser Val Lys
1               5                   10                  15

Met Ser Cys Lys Ala Ser Gly Tyr Thr Phe Thr Ser Tyr Thr Met His
            20                  25                  30

Trp Val Lys Gln Arg Pro Gly Gln Gly Leu Glu Trp Ile Gly Tyr Ile
        35                  40                  45

Asn Pro Ser Ser Gly Phe Thr Asn Tyr Asn Gln Lys Phe Lys Asp Lys
    50                  55                  60

Ala Thr Leu Thr Ala Asp Lys Ser Ser Ser Thr Ala Tyr Met Gln Leu
65                  70                  75                  80

Ser Ser Leu Thr Ser Glu Asp Ser Ala Val Tyr Tyr Cys Ala Arg Ser
                85                  90                  95

Arg Phe Ala Tyr Trp Gly Gln Gly Thr Leu Val Thr Val Ser Ala Ala
            100                 105                 110

Lys Thr Thr Pro Pro Ser
        115

<210> SEQ ID NO 65
<211> LENGTH: 118
<212> TYPE: PRT
<213> ORGANISM: Artificial Sequence
<220> FEATURE:
<223> OTHER INFORMATION: heavy chain sequence H3-2

<400> SEQUENCE: 65

Leu Gln Gln Ser Gly Ala Glu Leu Ala Arg Leu Gly Ala Ser Val Lys
1               5                   10                  15

Met Ser Cys Lys Ala Ser Gly Tyr Thr Phe Thr Ser Tyr Thr Met His
            20                  25                  30

Trp Val Lys Gln Arg Pro Gly Gln Gly Leu Glu Trp Ile Gly Tyr Ile
        35                  40                  45

Asn Pro Ser Ser Gly Phe Thr Asn Tyr Asn Gln Lys Phe Lys Asp Lys
    50                  55                  60

Ala Thr Leu Thr Ala Asp Lys Ser Ser Ser Thr Ala Tyr Met Gln Leu
65                  70                  75                  80

Ser Ser Leu Thr Ser Glu Asp Ser Ala Val Tyr Tyr Cys Ala Arg Ser
                85                  90                  95

Arg Phe Ala Tyr Trp Gly Gln Gly Thr Leu Val Thr Val Ser Ala Ala
            100                 105                 110

Lys Thr Thr Pro Pro Ser
        115

<210> SEQ ID NO 66
<211> LENGTH: 118
<212> TYPE: PRT
<213> ORGANISM: Artificial Sequence
<220> FEATURE:
<223> OTHER INFORMATION: heavy chain sequence H3-4

<400> SEQUENCE: 66

Leu Gln Gln Ser Gly Ala Glu Leu Ala Arg Pro Gly Ala Ser Val Lys
1               5                   10                  15

Met Ser Cys Lys Ala Ser Gly Tyr Thr Phe Thr Ser Tyr Thr Met His
            20                  25                  30

Trp Val Lys Gln Arg Pro Gly Gln Gly Leu Glu Trp Ile Gly Tyr Ile
        35                  40                  45

Asn Pro Ser Ser Gly Phe Thr Asn Tyr Asn Gln Lys Phe Lys Asp Lys
    50                  55                  60

Ala Thr Leu Thr Ala Asp Lys Ser Ser Ser Thr Ala Tyr Met Gln Leu
65                  70                  75                  80

Ser Ser Leu Thr Ser Glu Asp Ser Ala Val Tyr Tyr Cys Ala Arg Ser
                85                  90                  95

Arg Phe Ala Tyr Trp Gly Gln Gly Thr Leu Val Thr Val Ser Ala Ala
            100                 105                 110

Lys Thr Thr Pro Pro Ser
        115

<210> SEQ ID NO 67
<211> LENGTH: 121
<212> TYPE: PRT
<213> ORGANISM: Artificial Sequence
<220> FEATURE:
<223> OTHER INFORMATION: heavy chain sequence H5-2

<400> SEQUENCE: 67

Glu Val Gln Leu Leu Glu Thr Gly Ala Glu Leu Ala Arg Pro Gly Ala
1               5                   10                  15

Ser Val Lys Met Ser Cys Lys Ala Ser Gly Tyr Thr Phe Thr Ser Tyr
            20                  25                  30

Thr Met His Trp Val Lys Gln Arg Pro Gly Gln Gly Leu Glu Trp Ile
        35                  40                  45

Gly Tyr Ile Asn Pro Ser Ser Gly Phe Thr Asn Tyr Asn Gln Lys Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
            85                  90                  95

Ala Arg Ser Arg Phe Ala Tyr Trp Gly Gln Gly Thr Leu Val Thr Val
            100                 105                 110

Ser Ala Ala Lys Thr Thr Pro Pro Ser
            115                 120

<210> SEQ ID NO 68
<211> LENGTH: 121
<212> TYPE: PRT
<213> ORGANISM: Artificial Sequence
<220> FEATURE:
<223> OTHER INFORMATION: heavy chain sequence H5-3

<400> SEQUENCE: 68

Glu Val Gln Leu Leu Glu Thr Gly Ala Glu Leu Ala Arg Pro Gly Ala
1               5                   10                  15

Ser Val Lys Met Ser Cys Lys Ala Ser Gly Tyr Thr Phe Thr Ser Tyr
            20                  25                  30

Thr Met His Trp Val Lys Gln Arg Pro Gly Gln Gly Leu Glu Trp Ile
            35                  40                  45

Gly Tyr Ile Asn Pro Ser Ser Gly Phe Thr Asn Tyr Asn Gln Lys Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
            85                  90                  95

Ala Arg Ser Arg Phe Ala Tyr Trp Gly Gln Gly Thr Leu Val Thr Val
            100                 105                 110

Ser Ala Ala Lys Thr Thr Pro Pro Ser
            115                 120

<210> SEQ ID NO 69
<211> LENGTH: 121
<212> TYPE: PRT
<213> ORGANISM: Artificial Sequence
<220> FEATURE:
<223> OTHER INFORMATION: heavy chain sequence H6-1

<400> SEQUENCE: 69

Glu Val Gln Leu Gln Gln Ser Val Ala Glu Leu Ala Arg Pro Gly Ala
1               5                   10                  15

Ser Val Lys Met Ser Cys Lys Ala Ser Gly Tyr Thr Phe Thr Ser Tyr
            20                  25                  30

Thr Met His Trp Val Lys Gln Arg Pro Gly Gln Gly Leu Glu Trp Ile
            35                  40                  45

Gly Tyr Ile Asn Pro Ser Ser Gly Phe Thr Asn Tyr Asn Gln Lys Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
            85                  90                  95

Ala Arg Ser Arg Phe Ala Tyr Trp Gly Gln Gly Thr Leu Val Thr Val
            100                 105                 110

Ser Ala Ala Lys Thr Thr Pro Pro Ser
            115                 120

-continued

```
<210> SEQ ID NO 70
<211> LENGTH: 121
<212> TYPE: PRT
<213> ORGANISM: Artificial Sequence
<220> FEATURE:
<223> OTHER INFORMATION: heavy chain sequence H6-3

<400> SEQUENCE: 70

Glu Val Gln Leu Gln Gln Ser Val Ala Glu Leu Ala Arg Pro Gly Ala
 1               5                  10                  15

Ser Val Lys Met Ser Cys Lys Ala Ser Gly Tyr Thr Phe Thr Ser Tyr
            20                  25                  30

Thr Met His Trp Val Lys Gln Arg Pro Gly Gln Gly Leu Glu Trp Ile
        35                  40                  45

Gly Tyr Ile Asn Pro Ser Ser Gly Phe Thr Asn Tyr Asn Gln Lys Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Arg Phe Ala Tyr Trp Gly Gln Gly Thr Leu Val Thr Val
            100                 105                 110

Ser Ala Ala Lys Thr Thr Pro Pro Ser
        115                 120

<210> SEQ ID NO 71
<211> LENGTH: 121
<212> TYPE: PRT
<213> ORGANISM: Artificial Sequence
<220> FEATURE:
<223> OTHER INFORMATION: heavy chain sequence H7-4

<400> SEQUENCE: 71

Gln Val His Leu Gln Gln Ser Gly Ala Glu Leu Ala Arg Pro Gly Ala
 1               5                  10                  15

Ser Val Lys Met Ser Cys Lys Ala Ser Gly Tyr Thr Phe Thr Ser Tyr
            20                  25                  30

Thr Met His Trp Val Lys Gln Arg Pro Gly Gln Gly Leu Glu Trp Ile
        35                  40                  45

Gly Tyr Ile Asn Pro Ser Ser Gly Phe Thr Asn Tyr Asn Gln Lys Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Arg Phe Ala Tyr Trp Gly Gln Gly Thr Leu Val Thr Val
            100                 105                 110

Ser Ala Ala Lys Thr Thr Pro Pro Ser
        115                 120

<210> SEQ ID NO 72
<211> LENGTH: 121
<212> TYPE: PRT
<213> ORGANISM: Artificial Sequence
<220> FEATURE:
<223> OTHER INFORMATION: heavy chain sequence H7-6

<400> SEQUENCE: 72

Gln Val His Leu Gln Gln Ser Ala Ala Glu Leu Ala Arg Pro Gly Ala
 1               5                  10                  15
```

```
Ser Val Lys Met Ser Cys Lys Ala Ser Gly Tyr Thr Phe Thr Ser Tyr
            20                  25                  30

Thr Met His Trp Val Lys Gln Arg Pro Gly Gln Gly Leu Glu Trp Ile
        35                  40                  45

Gly Tyr Ile Asn Pro Ser Ser Gly Phe Ala Asn Tyr Asn Gln Lys Phe
        50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Arg Phe Ala Tyr Trp Gly Gln Gly Thr Leu Val Thr Val
            100                 105                 110

Ser Ala Ala Lys Thr Thr Pro Pro Ser
            115                 120

<210> SEQ ID NO 73
<211> LENGTH: 17
<212> TYPE: PRT
<213> ORGANISM: Artificial Sequence
<220> FEATURE:
<223> OTHER INFORMATION: heavy chain sequence after stop codon

<400> SEQUENCE: 73

Val Arg Arg Pro Cys Leu Leu Gly Pro Arg Asp Ser Gly His Cys Leu
1               5                   10                  15

Cys
```

HUMANIZED ANTI-EMAP II ANTIBODY AND USE THEREOF

RELATED APPLICATIONS

This application is the National Stage of International Application. No. PCT/KR2011/005203, filed 14 Jul. 2011, which claims benefit of priority to Korean Patent Application No. 10-2011-0036569, filed 20 Apr. 2011, the specification of which is incorporated by reference herein.

TECHNICAL FIELD

The present invention relates to a humanized anti-EMAP II antibody and the use thereof.

BACKGROUND ART

Endothelial monocyte activating polypeptide II (EMAP II) is a polypeptide isolated from methylcholanthrene A-transformed fibrosarcoma cells (Kao et al., J. Biol. Chem. 267: 20239-20247, 1992). It is known to inhibit the growth of primary and metastatic tumors and induce apoptosis in proliferating endothelial cells (Schwarz et al., J. Exp. Med. 190: 341-353, 1999).

EMAP II is released from the precursor protein p43 during apoptosis. The precursor p43 (pro-EMAP II) protein consists of 312 amino acids and is associated with the multi-tRNA synthetase complex in eukaryotes (Park et al., J. Biol. Chem. 274:16673-166776, 1999). However, it is cleaved to release its C-terminal domain by an activated caspase-7 during apoptosis and to generate EMAP-II (Behrensdorf et al., FEBS Lett. 466:143-147, 2000).

It is known that the EMAP II protein shows sequence similarity with domains present in a variety of different aminoacyl-tRNA synthetases (Quevillon et al., J. Biol. Chem. 272; 32573-32579, 1997) and can bind with tRNA. Also, it is known that 15 peptides at the N-terminal end are involved in the cytokine activity of EMAP II (Kao et al. J. Biol. Chem. 269:9774-9782, 1994).

EMAP II is a mediator of proinflammatory responses that induces the expression of tissue factor, tumor necrosis factor (hereinafter referred to as "TNF") and interleukin-8 (hereinafter referred to as "IL-8") in mononuclear phagocyte and polymorphonuclear leucocytes. Also, in a tissue expressing a high level of EMAP II mRNA, macrophages are accumulated. This means that EMAP II is a chemotaxis material directing macrophage to dead cells. It is known that EMAP II acts as a cytokine, and 15 amino acids at the N-terminal domain of EMAP II play a significant role (Quevillon, S. et al., J. Biol. Chem., 272:32573-32579, 1997; Kao, J. et al., J. Biol. Chem., 269:9774-7982, 1994; Kao, J. et al., J. Biol. Chem., 267:20239-20247, 1992; Kao, J. et al., J. Biol. Chem., 269:25106-25119, 1994; Knies, U. E. et al., PNAS USA, 95:12322-12327, 1998). In U.S. Pat. No. 5,641,867 discloses that the N-terminal domain of an EMAP II comprising arginine-isoleucine-glycine-arginine-isoleucine-threonine is an important residue in the cytokine function of the EMAP II. Recently, it was reported that EMAP II repressed the growth of primary and metastatic tumors in proliferating endothelial cells while it did not cause particular side effects in normal cells (Schwarz, M. A. et al., J. Exp. Med., 190:341-353, 1999).

Meanwhile, p43 known as the precursor of EMAP II is known to be expressed extensively. The expression level of p43 protein varies temporally and spatially, especially in a developing mouse. For example, it was shown that the expression of p43 in the lung of 8-16-day-old mice was increased dramatically. In addition, p43 is highly expressed in the microglial cells in the lesions of autoimmune disease such as encephalomyelitis, neuritis and uveitis. The high expression level of p43 in specific developmental stages and tissues suggests that p43 involves inflammation and apoptosis (Tas, M. P. R., and Marray, J. C., Int. J. Biochem. Cell. Biol., 28:837-841, 1996; Schwarz, M. J. et al., Glia, 20:365-372, 1997; Schuesner, H. J. et al., Glia, 20:365-372, 1997; Berger, A. C. et al., J. Immunother., 23:519-527, 2000).

Previously, the present inventor found that monoclonal antibodies specific for EMAP II can be used for the diagnosis and treatment of inflammatory diseases, inhibits the secretion of TNF-α mediating inflammatory responses and is effective for the treatment of Alzheimer's disease (Korean Patent Laid-Open Publication No. 10-2010-0093451).

DISCLOSURE

Technical Problem

Monoclonal antibodies (mAbs) have enormous potential as therapeutic agents. However, non-human antibodies are highly immunogenic in the human body and their short half-life severely limits their clinical efficacy.

Technical Solution

Accordingly, the present inventor has made many efforts to solve the above-described problem of the humanized antibody and, as a result, has prepared an EMAP II-specific humanized antibody which has minimized immunogenicity while having similar or improved antigen-binding capacity compared to the parent monoclonal antibody that binds specifically to EMAP II, thereby completing the present invention.

One aspect of the present invention provides a humanized anti-EMAP II antibody that binds specifically to EMAP II.

Another aspect of the present invention provides the use of the humanized anti-EMAP II antibody.

Still another aspect of the present invention provides a pharmaceutical composition including the humanized anti-EMAP II antibody.

Mouse-derived antibodies induce undesired immune responses in humans, because they act as antigens in humans so that new human anti-mouse antibodies (HAMAs) against the mouse-derived antibodies are produced. To overcome this problem, proposals have been made for reducing the immunogenicity of non-human antibodies in humans. Such techniques can be generically termed "humanization" techniques. These techniques generally involve the use of recombinant DNA technology to manipulate DNA sequences encoding the polypeptide chains of the antibody molecule. Early methods for preparing humanized antibodies involved production of chimeric antibodies in which an antigen binding site comprising the complete variable domains of a non-human antibody is linked to constant domains derived from a human antibody.

Accordingly, the present invention provides a chimeric anti-EMAPII antibody comprising: a light-chain variable domain having an amino acid sequence set forth in SEQ ID NO: 11; and a heavy-chain variable domain having an amino acid sequence set forth in SEQ ID NO: 19.

The present invention also provides a humanized form of the chimeric anti-EMAPII antibody.

Specifically, the present invention provides a humanized anti-EMAPII (endothelial monocyte activating polypeptide II) comprising: (i) a light-chain variable domain having an amino acid sequence set forth in any one of SEQ ID NO: 12 to SEQ ID NO: 18; and (ii) a heavy-chain variable domain having an amino acid sequence set forth in any one of SEQ ID NO: 20 to SEQ ID NO: 26.

In one embodiment, the present invention provides a humanized anti-EMAPII antibody comprising: a light-chain variable domain having an amino acid sequence set forth in SEQ ID NO: 12, and a heavy-chain variable domain having an amino acid sequence set forth in SEQ ID NO: 20; a light-chain variable domain having an amino acid sequence set forth in SEQ ID NO: 13, and a heavy-chain variable domain having an amino acid sequence set forth in SEQ ID NO: 21; a light-chain variable domain having an amino acid sequence set forth in SEQ ID NO: 14, and a heavy-chain variable domain having an amino acid sequence set forth in SEQ ID NO: 22; a light-chain variable domain having an amino acid sequence set forth in SEQ ID NO: 15, and a heavy-chain variable domain having an amino acid sequence set forth in SEQ ID NO: 23; a light-chain variable domain having an amino acid sequence set forth in SEQ ID NO: 16, and a heavy-chain variable domain having an amino acid sequence set forth in SEQ ID NO: 24; a light-chain variable domain having an amino acid sequence set forth in SEQ ID NO: 17, and a heavy-chain variable domain having an amino acid sequence set forth in SEQ ID NO: 25; or a light-chain variable domain having an amino acid sequence set forth in SEQ ID NO: 18, and a heavy-chain variable domain having an amino acid sequence set forth in SEQ ID NO: 26.

As used herein, the term "humanized antibody" generally means an antibody that is non-immunogenic in humans or has reduced immunogenicity in humans. A humanized antibody is an antibody having an altered amino acid sequence, and the amino acid sequence of the antibody may be reconstituted according to intended purposes. A large number of changes are possible, which range from changes of one or several amino acids to complete reconstitution of variable and/or constant regions of an antibody.

As used herein, the term "variable domain" means a portion of an antibody molecule, which functions to bind specifically to an antigen and shows many variations in its sequence. Complementarity determining regions, CDR1, CDR2 and CDR3, are present in a variable domain. The term "complementarity determining regions (CDRs)" means loop-like regions which participate in antigen recognition and in which the specificity of an antibody for an antigen is determined according to changes in the sequences of CDRs.

The present invention also provides a humanized anti-EMAPII antibody comprising, in addition to said light-chain variable domain and heavy-chain variable domain, a human IgG1-derived constant domain.

The present invention also provides a pharmaceutical composition comprising said humanized anti-EMAPII antibody.

The present invention also provides a kit for quantification of EMAPII comprising said humanized anti-EMAPII antibody.

The present invention also provides a nucleic acid molecule encoding a light-chain variable domain having an amino acid sequence set forth in any one SEQ ID NO: 12 to SEQ ID NO: 18.

The present invention also provides a nucleic acid molecule encoding a heavy-chain variable domain having an amino acid sequence set forth in any one SEQ ID NO: 20 to SEQ ID NO: 26.

The present invention also provides a recombinant vector comprising nucleic acid molecules encoding said light-chain variable domain and heavy-chain variable domain.

The present invention also provides a transformed cell comprising said recombinant vector.

The present invention also provides a method of producing said humanized antibody by culturing said transformed cell.

"Humanized forms of non-human (e.g., murine) antibodies are chimeric antibodies which contain minimal sequence derived from non-human immunoglobulin. In most instances, humanized antibodies are human immunoglobulins (recipient antibody) in which hypervariable region residues of the recipient are replaced by hypervariable region residues from a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Reichmann et al., Nature 332:323-329 (1988); and Presta, Curr. Op. Struct. Biol. 2:593-596 (1992).

Methods for humanizing non-human antibodies are well known in the art, and a humanized antibody has one or more amino acid residues introduced into it from a source which is non-human. Humanization can be essentially performed following the method of Winter and co-workers (Jones et al., Nature, 321:522-525 (1986); Riechmann et al., Nature, 332: 323-327 (1988); Verhoeyen et al., Science, 239:1534-1536 (1988)), by substituting CDR sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. Typically, humanized antibodies are human antibodies in which some CDR residues and possibly some FR residues are substituted by residues from analogous sites in rodent antibodies.

The choice of human variable domains, both light and heavy chains, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., J. Immunol., 151:2296 (1993); Chothia et al., J. Mol. Biol., 196:901 (1987)). Another method uses a particular framework derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immunol., 151:2623 (1993)).

It is also important to humanize antibodies with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the residues in the hypervariable region are directly and most substantially involved in influencing antigen binding.

Modifications of the antibody are also contemplated in the present invention. For example, the antibody can be linked to one of a variety of nonproteinaceous polymers, e.g., polyethylene glycol, polypropylene glycol, polyoxyalkylenes, or copolymers of polyethylene glycol and polypropylene glycol.

The antibody also can be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules), or in macroemulsions. Such techniques are disclosed in Remington's Pharmaceutical Sciences, 16th edition, Oslo, A., Ed., (1980).

The anti-EMAP II antibody of the present invention can be formulated as immunoliposomes. Liposomes containing the antibody can be prepared by methods known in the art, such as described in Epstein et al., Proc. Natl. Acad. Sci. USA 82:3688 (1985); Hwang et al., Proc. Natl. Acad. Sci. USA 77:4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem. 257: 286-88 (1982) via a disulfide interchange reaction. A chemotherapeutic agent is optionally contained within the liposome (Gabizon et al. J. National Cancer Inst. 81 (19) 1484 (1989)).

The present invention also provides an isolated nucleic acid encoding the humanized anti-EMAP II antibody, a recombinant vector containing the nucleic acid, a transformed cell comprising the recombinant vector and a recombinant technique for producing the antibody.

For recombinant production of the antibody, the nucleic acid encoding it is isolated and inserted into a replicable vector for further cloning (amplification of the DNA) or for expression. DNA encoding the monoclonal antibody is readily isolated and sequenced using conventional procedures (e.g., by using oligonucleotide probes that are capable of binding specifically to genes encoding the heavy and light chains of the antibody). Conventional vectors known in the art are available. The vector components generally include, but are not limited to, one or more of a signal sequence, an origin of replication, one or more marker genes, an enhancer element, a promoter, and a transcription termination sequence.

The present invention also provides a microbial or animal cell transformed with said recombinant vector. A microbial or animal cell that can be transformed with the vector in the present invention may be a known microbial or animal cell for transformation which is used in the art.

The present invention also provides pharmaceutical formulations comprising the humanized anti-EMAP II antibody. The pharmaceutical formulations of the present invention are prepared for storage by mixing the antibody that has the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The humanized anti-EMAPII antibody of the present invention effectively inhibits the secretion of TNF-α, and thus can be used for prevention or treatment of TNF-α-mediated diseases.

TNF-α-mediated diseases include adult respiratory distress syndrome; anorexia; cancer (e.g., leukemia); chronic fatigue syndrome; graft versus host rejection; hyperalgesia; inflammatory bowel disease; neuroinflammatory diseases; ischemic/reperfusion injury, including cerebral ischemia (brain injury as a result of trauma, epilepsy, hemorrhage or stroke, each of which may lead to neurodegeneration); diabetes (e.g., juvenile onset Type 1 diabetes mellitus); multiple sclerosis; ocular diseases; pain; pancreatitis; pulmonary fibrosis; rheumatic diseases (e.g., rheumatoid arthritis, osteoarthritis, juvenile (rheumatoid) arthritis, seronegative polyarthritis, ankylosing spondylitis, Reiter's syndrome and reactive arthritis, psoriatic arthritis, enteropathic arthritis, polymyositis, dermatomyositis, scleroderma, systemic sclerosis, vasculitis, cerebral vasculitis, Sjogren's syndrome, rheumatic fever, polychondritis and polymyalgia rheumatica and giant cell arteritis); septic shock; side effects from radiation therapy; systemic lupus erythematous; temporal mandibular joint disease; and thyroiditis.

In addition, the humanized anti-EMAPII antibody of the present invention can be used for prevention or treatment of Alzheimer's disease.

The anti-EMAPII antibody of the present invention can be administered to a human patient by a known method in a bolus dose or by continuous injection over a certain period of time, for example, via an intravenous, intramuscular, intraperitoneal, intracerebral, subcutaneous, intraarticular, intrasynovial, intrasubarachnoidal, oral, local, or inhalation route. In a preferred embodiment, the antibody is administered intravenously or subcutaneously.

For the prevention or treatment of disease, the appropriate dosage of the antibody will depend on the type of disease to be treated, as defined above, the severity and course of the disease, previous therapy, the patient's clinical history and response to the antibody, and the discretion of the attending physician. The antibody is suitably administered to the patient at one time or over a series of treatments. Depending on the type and severity of the disease, about 10 µg/kg to 5 mg/kg of the antibody is an initial candidate dosage for administration to the patient, whether, for example, by one or more separate administrations, or by continuous infusion. The typical daily dose of the humanized anti-EMAPII antibody of the present invention may range from 10 µg/kg to 5 mg/kg depending on the above-mentioned factors. For repeated administrations over several days or longer, depending on the condition, the treatment is repeated until a desired suppression of disease symptoms is achieved. The preferred dosage of the antibody will be in the range from about 1 mg/kg to about 2 mg/kg. Thus, one or more doses of about 0.5 mg/kg, 1 mg/kg or 2 mg/kg (or any combination thereof) may be administered to the patient.

Aside from administration of the antibody protein to the patient, the present invention contemplates administration of the antibody by gene therapy. See, for example, WO 96/07321 published Mar. 14, 1996 concerning the use of gene therapy to generate intracellular antibodies.

The present invention also provides an article containing the humanized anti-EMAPII antibody. This article comprises a container and a label or package insert on or associated with the container. Suitable containers include, for example, bottles, vials or syringes. The composition of the present invention may be placed into a container with a sterile access port, for example, an intravenous solution bag or vial having a stopper pierceable by a hypodermic injection needle.

The humanized anti-EMAPII antibody of the present invention may also be used for non-therapeutic purposes.

For example, the antibody of the present invention may be used as affinity purification agents. In this process, the antibody is immobilized on a suitable support, such a Sephadex resin or filter paper, using methods well known in the art. The immobilized antibody is contacted with a sample containing EMAP II protein (or a fragment thereof) to be purified, and then the support is washed with a suitable solvent that will remove substantially all the material in the sample except the EMAP II protein, which is bound to the immobilized antibody. Finally, the support is washed with another suitable solvent, such as glycine buffer (pH 5.0) that will release the EMAP II protein from the antibody.

Also, the anti-EMAPII antibody may be useful for a diagnostic assay for EMAPII protein, for example, for detecting the expression of EMAPII protein in a specific cell, tissue or serum.

When the antibody is used for diagnosis, it will be labeled with detectable labels. Such labels include: (a) radioactive isotopes such as $^{35}$S $^{14}$C, $^{125}$I, $^{3}$H and $^{131}$I (see, for example, Current Protocols in Immunology, Volumes 1 and 2, Coligen et al., Ed. Wiley-Interscience, New York, N.Y., Pubs. (1991)); (b) fluorescent labels, including rare earth chelates (europium chelates) or fluorescein and its derivatives, rhodamine and its derivatives, dansyl, Lissamine, phycoerythrin and Texas Red (see, for example, Current Protocols in Immunology, supra); (c) enzymatic labels, including luciferases (e.g., firefly luciferase and bacterial luciferase; U.S. Pat. No. 4,737,456), luciferin, 2,3-dihydrophthalazinediones, malate dehydrogenase, urease, peroxidase (e.g., horseradish peroxidase (HRPO)), alkaline phosphatase, β-galactosidase, glucoamylase, lysozyme, saccharide oxidases (e.g., glucose oxidase, galactose oxidase, and glucose-6-phosphate dehydrogenase), heterocydic oxidases (such as uricase and xanthine oxidase), lactoperoxidase, microperoxidase, and the like (see, for example, U.S. Pat. No. 4,275,149, O'Sullivan et al., Methods for the Preparation of Enzyme-Antibody Conjugates for use in Enzyme Immunoassay, in Methods in Enzym. (ed J. Langone & H. Van Vunakis), Academic press, New York, 73:147-166 (1981)).

The detectable label can be indirectly conjugated with the antibody. For example, the antibody can be conjugated with biotin and any of the three broad categories of labels mentioned above can be conjugated with avidin, or vice versa. Biotin binds selectively to avidin, and thus the label can be conjugated with the antibody in this indirect manner. Alternatively, to achieve indirect conjugation of the label with the antibody, the antibody is conjugated with a small hapten (e.g., digoxin) and one of the different types of labels mentioned above is conjugated with an anti-hapten antibody (e.g., anti-digoxin antibody). Thus, indirect conjugation of the label with the antibody can be achieved.

Additionally, the antibody of the present invention needs not be labeled, and the presence thereof can be detected using a labeled antibody which binds to the antibody of the present invention.

The antibody of the present invention may be employed in any known assay method, such as competitive binding assays, direct and indirect sandwich assays, and immunoprecipitation assays (Zola, Monoclonal Antibodies: A Manual of Techniques, at pp. 147-158 (CRC Press, Inc. 1987)).

For immunohistochemistry, a tissue sample may be fresh or frozen or may be embedded in paraffin and fixed with a preservative such as formalin.

The antibody of the present invention may also be used for in vivo diagnostic assays. Generally, the antibody is labeled with a radio nuclide (such as $^{111}$In, $^{99}$Tc, $^{14}$C, $^{131}$I, $^{125}$I, $^{3}$H, $^{32}$P or $^{35}$S) so that tumors can be localized using immunoscintiography.

As a matter of convenience, the antibody of the present invention can be provided in a kit, i.e., a packaged combination of reagents in predetermined amounts in one or more containers with instructions for performing the diagnostic assay. Where the antibody is labeled with an enzyme, the kit will include substrates and co factors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

Advantageous Effects

The humanized anti-EMAP II antibody of the present invention, which binds specifically to EMAP II, shows reduced immunogenicity and increased half-life while having similar or improved antigen binding capacity compared to the parent monoclonal antibody. Thus, the humanized anti-EMAP II antibody of the present invention can be more effectively used as a diagnostic reagent for EMAP II and a therapeutic agent for diseases that are mediated by EMAP II.

DESCRIPTION OF DRAWINGS

FIG. 5 shows the results of sequencing a PCR product obtained using a primer combination of mK2 and mK3 (Genbank entry AAA39004 (SEQ ID NO: 27); K2-1-T7 (SEQ ID NO:35); K2-2-T7 (SEQ ID NO:36); K2-3-T7 (SEQ ID NO:37); K2-4-T7 (SEQ ID NO:38); K2-5-T7 (SEQ ID NO:39); K2-6-T7 (SEQ ID NO:40); K3-2-T7 (SEQ ID NO:41); K3-4-T7 (SEQ ID NO:42); K3-5-T7 (SEQ ID NO:43); and K3-6-T7 (SEQ ID NO:44)).

FIG. 6 shows the results of sequencing clones induced using the primers mk6, mK7, mK8, mK9 and mK11 (aligned with the mouse embryonic gene Vk 19-17 (SEQ ID NO: 28)); K6-2 (SEQ ID NO:45); K6-1 (SEQ ID NO:46); K7-3 (SEQ ID NO:47); K7-6 (SEQ ID NO:48); K8-1 (SEQ ID NO:49); K8-2 (SEQ ID NO:50); K9-1 (SEQ ID NO:51); K9-5 (SEQ ID NO:52); K11-1 (SEQ ID NO:53); K11-3 (SEQ ID NO:54); K11-4 (SEQ ID NO:55); and K11-5 (SEQ ID NO:56)).

FIG. 7 shows the results of performing variable-domain PCR using gene-specific primers.

FIG. 8 shows the DNA sequences (SEQ ID NOS: 31 and 32) and deduced amino acid sequence (SEQ ID NO: 5) of a light-chain variable domain, obtained by PCR.

FIG. 9 shows the results of sequencing a variable-domain PCR product (SEQ ID NO: 29) obtained using the primer H4 (H4-4 (SEQ ID NO:57); H4-5 (SEQ ID NO:58); and H4-6 (SEQ ID NO:59). In the sequences H4-4, H4-5 and H4-6, the stop codon was followed by a sequence encoding VRRP-CLLGPRDSGHCLC (SEQ ID NO:73)).

FIG. 10 shows the results of sequencing clones induced using a primer combination of H1, H2, H3, H5, H6 and H7 (aligned with the mouse embryonic gene Vh1-4*1 (SEQ ID NO: 30): H1-1 (SEQ ID NO:60); H1-2 (SEQ ID NO:61); H1-3 (SEQ ID NO:62); H2-4 (SEQ ID NO:63); H3-1 (SEQ ID NO:64); H3-2 (SEQ ID NO:65); H3-4 (SEQ ID NO:66); H5-2 (SEQ ID NO:67); H5-3 (SEQ ID NO:68); H6-1 (SEQ ID NO:69); H6-3 (SEQ ID NO:70); H7-4 (SEQ ID NO:71); and H7-6 (SEQ ID NO:72)).

FIG. 11 shows the DNA sequences (SEQ ID NOS: 33 and 34) and deduced amino acid sequence (SEQ ID NO: 6) of a heavy-chain variable domain, obtained by PCR.

MODE FOR INVENTION

Figure 1:
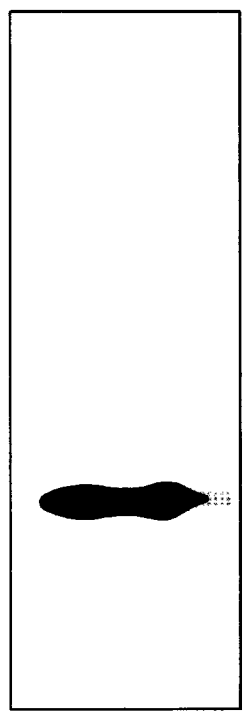
FIG. 1 shows the results of confirming that a monoclonal antibody cell line of the present invention is specific for EMAPII.

Hereinafter, the present invention will be described in detail with reference to examples. It is to be understood, however, that these examples are for illustrative purposes only and are not to be construed to limit the scope of the present invention.

EXAMPLES

Example 1

Manufacturing of Monoclonal Anti-EMAPII Antibody-Producing Hybridoma (1) Cloning EMAPII and Separation of Protein ORF (1-312aa) encoding human EMAPII (SEQ ID No. 1) was amplified by using primer; F: 5'-GCGAATTCATG-GCAAATAATGATGCTGTTC-3' (SEQ ID No. 2), R: 5'-CCGCTCGAGTTATTTGATTCCACTGTTGCTCATG-3' (SEQ ID NO. 3) from HEK293 cDNA and performing 25 cycles of 95° C. 1 min, 55° C. 1 min and 72° C. 1 min. The PCR product was restricted by EcoRI/SalI, and ligased with pGEX4T-1 vector (Pharmacia), formerly restricted with EcoRI/SalI, for 2 hours at room temperature. After transformation of DH-5a by heat shock for 90 sec at 42° C., the *E. coli* was cultured in LB media containing ampiciline (50 μg/ml), and colonies including EMAPII were selected. The cloned EMAPII gene was sequenced and there was no mutation.

After transformation of *E. coli* BL21 (DE3) with EMAPII plasmid, the *E. coli* was plated to LB media containing ampiciline (50 μg/ml), and cultured for 24 hours at 37° C. The grown colony was cultured in 5 ml of LB media containing ampiciline (50 μg/ml) for 12 hours, and then 4 ml of the cultured media was inoculated to 2 L of LB media containing ampiciline (50 μg/ml). It was cultured at 37° C. until O.D (600 nm) reached 0.3. IPTG was added in a final concentration of 0.1 mM, and p43 protein was expressed by culturing for 6 hours at 30° C. After *E. coli* was centrifuged for 15 min at 7,000 rpm, the cells were resuspended by 1×PBS (8 g NaCl, 0.2 g KCl, 1.44 g $Na_2HPO$, 0.24 g $KH_2PO_4$/L, pH 7.4), sonicated at 4° C. and centrifuged at 4° C. for 40 min at 26,000×g. The supernatant was obtained and loaded to a glutathione Sepharose 4B-column which becomes homogeneous by 1×PBS. The resin was washed with PBS, and GST-p43 was eluted by using 50 mM of Tris-HCl (pH 8.0) containing 10 mM of glutathione. The purity was identified by using 10% SDS-PAGE. The purity was over 90% on SDS-PAGE. The dialysis was performed by using PBS containing 20% glycerol, and the dialyzed product was stored at −70° C.

(2) Preparation of the EMAPII Antibody Monoclone Cell Line

1) Antigen Immunization

An emulsion was prepared by mixing 20 μg/mouse of the protein with the same volume of Complete Freund's Adjuvant (Sigma, USA). The emulsion was intraperitoneally injected into three 7-week-old female Balb/c mice (orient). 20 μg of antigen was injected into each mouse with the 400 μl of total volume. After 2 weeks, the emulsion mixing Incomplete Freund's Adjuvant (Sigma, USA) and antigen was intraperitoneally injected into the mouse. After 2 weeks, the antigen (20 μg/mouse) dissolved in PBS was intraperitoneally injected to induce the production of antibody. After identifying the antibody by performing enzyme immunoassay and western blot analysis, antigen dissolved in PBS was further injected into a tail vein of the mouse 3 days before the cell fusion.

2) Identifying and Screening the Cells Producing Antibody

Blood was obtained from the eye ball of an immunized mouse according to the above method, placed into the 1.5 ml microcentrifuge tube and centrifuged for 10 min at 13,000 rpm. The serum was separated and stored at −20° C. until the experiment for identifying the production of antibody was performed. After identifying the production of antibody by performing enzyme immunoassay and western blot analysis using antigen protein, the fusion for spleen cells of the antibody-producing mouse was performed.

3) Preparation of Hybridoma Cell

After the production of the antibody was identified, the mouse was sacrificed and the splenocytes were separated. The splenocytes were fused with myeloma cells P3X63Ag8.653 (ATCC CRL-1580, USA). That is, P3X63Ag8.653 cells of the mouse were maintained in the culture plate by using RPMI1640 media supplemented with 10% fetal bovine serum. To perform the cell fusion, P3X63Ag 8.653 cells were washed two times with serum-free RPMI1640 media (Biowhittaker, USA) and adjusted to become the concentration of $1 \times 10^7$ cells. The mouse was sacrificed by cervical dislocation, and its spleen was obtained. It was placed into the mesh (Sigma, USA) container, and the cells were separated. After making suspension of the spleen cells, the suspension was washed by centrifugation. The spleen cell solution was exposed to Tris-NH$_4$Cl solution (Tris 20.6 g/L, NH$_4$Cl 8.3 g/L) to lyse red blood cells. After the completely separated antibody-producing cells were centrifuged for 5 min at 400 g, they were washed two times with serum-free media and resuspended into the 10 ml media. The lymph cells were counted by using a haemocytometer, and $1 \times 10^8$ of lymphocytes were mixed with $1 \times 10^7$ of P3X63Ag 8.653 cells (10:1) in the serum-free media. The centrifugation was performed for 5 min at 400 g.

By using 50% (M/V) polyethylene glycol 1500 (Sigma, USA) pretreated at 37° C., 10 ml solution was dropped to mix for 1 min. The fusion mixture solution produced in the above was diluted with serum-free RPMI1640 and centrifuged for 3 min at 400 g. The cells were suspended in the 35 ml of RPMI1640 selection media supplemented with 20% fetal bovine serum and HAT (100 µM hypoxanthine, 0.4 µM aminopterin, 16 µM thymidine). 100 µl of the suspension solution was loaded to 96 well plates coated with feeder cells (macrophages separated from abdominal cavity using RPMI1640) one day before and cultured at 37° C., 5% CO$_2$. After 5 days, HAT selection media were replaced in 2 to 3 days intervals, and the cells were cultured for 14 days. After 14 days, subculture was performed by replacing RPMI1640 media supplemented with 20% fetal bovine serum and HT (media in which 0.4 µM aminopterine is removed from HAT media).

4) Selection and Separation of Fusion Cells Producing Each Antibody

The supernatant of the culture fused in the above was obtained, and the enzyme immunoassay was performed to investigate the production of the provided antigen-specific antibody (FIG. 1). The culture solution of fusion cells which represents the titer more than 4 times compared with negative control was selected and transferred to a 24-well culture plate and a 25 cm$^2$ culture flask.

5) Separation of Immunoglobulin and Determination of Isotype

Ascites obtained from the immunized mouse are mixed with protein G agarose (Invitrogen) and purification was carried out.

Using 10% SDS-PAGE, purity of IgG was confirmed and then, dialysis with PBS (20% glycerol) was performed and stored at −70° C.

Figure 2:
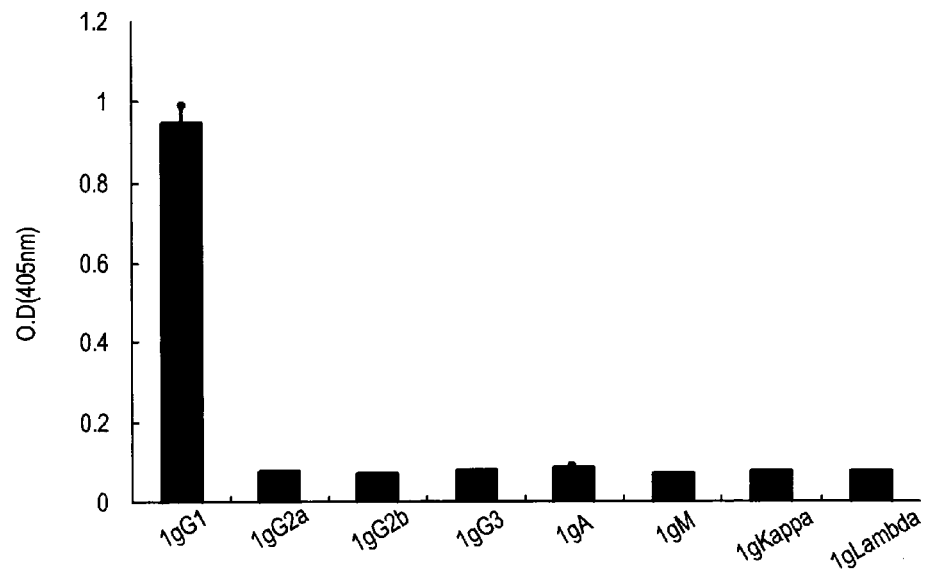
FIG. 2 shows the results of determining the isotype of the monoclonal antibody of the present invention.

Pristine 0.5 ml (Sigma, USA) was injected to mouse (Balb/c nu/nu, Charles River Diagnostics, Japan) intraperitoneally to increase frequency of peritoneal tumor and 7 days later, $5 \times 10^5$ fusion cells was injected intraperitoneally to induce ascites production. 10-14 days later, antibodies were isolated from the ascites. Monoclonal isotypes were determined with Isotyping kit (Zymed Labomouseories Inc. USA). As a result, the antibodies against EMAPII turned out to be IgG1 (FIG. 2).

Example 2

Cloning of Anti-EMAPII Antibody Variable Domains (1) cDNA Synthesis from Hybridoma Total RNA was prepared from $5 \times 10^5$ hybridoma cells. cDNA was synthesized with oligo dT primers and reverse transcriptase using protocol which is commercially available from BioAtla.

(2) PCR Amplification of Variable Domains of Mouse IgG

1) Light Chain Variable Domains

Figure 3:
FIG. 3 shows the results of PCR carried out using a combination of kappa-specific primers for the light-chain variable domain of mouse anti-EMAPII monoclonal antibody.

Kappa light chain variable domains were amplified from cDNA using a set of mouse specific kappa primers and amplification protocol which are commercially available from BioAtla. The forward primers are designed to amplify the mouse light chain variable domains in combination with a kappa specific reverse primer. Negative controls were performed at the same time by adding H$_2$O instead of cDNA. Seven different primer combinations (K2, K3, K6, K7, K8, K9, and K11; forward primer mK2, mK3, mK6, mK7, mK9 and mK11 in FIG. 3) resulted in a PCR product of the expected size (~430 bp) (FIG. 3). PCR products were gel purified, TOPO-TA cloned and sequenced (6 clones each).

2) Heavy Chain Variable Domain

Heavy chain variable domains were amplified from the above obtained cDNA using a set of mouse specific heavy chain primers and amplification protocol which are commercially available from BioAtla. The forward primers are designed to amplify the mouse heavy chain variable domains in combination with a mouse IgG1/2 specific reverse primer. Negative controls were performed at the same time by adding H$_2$O instead of cDNA. cDNA quality was checked by amplification of a 500 bp fragment of the mouse GAPDH.

Figure 4:
FIG. 4 shows the results of PCR carried out using a combination of heavy chain-specific primers for the heavy-chain variable domain of mouse anti-EMAPII monoclonal antibody.

7 different primer combinations (mH1-mH7) resulted in a PCR product of the expected size (~450 bp) (FIG. 4). PCR products were gel purified, TOPO-TA cloned and sequenced (6 clones each).

(3) Sequence Analysis of PCR Products after Cloning Using TOPO-TA Vector

The PCR products were TOPO TA cloned (Invitrogen TOPO TA vector) and sequenced using M13 forward primer (gtaaaacgacggccag: SEQ ID NO. 4).

1) Light Chain Variable Domain

Sequence analysis revealed that primer combinations mK2 and mK3 amplified the same light chain sequence (FIG. 5). The clones have a stop codon in the CDR3/Framework 4 region yielding a non productive V-J rearrangement. This sequence is commonly found in hybridomas made with fusion partners derived from the original MOPC-21 tumor.

Sequence analysis (Vector NTI, Invitrogen) of the clones derived with primers mk6, mK7, mK8, mK9, and mK11 showed that the same light chain sequence was amplified (FIG. 6). The obtained clones have only a few amino acid differences at the amino terminus which are introduced by ambiguities in the PCR primers. The sequences were blasted against the mouse genome. The mouse germ line gene Vk19-17 was identified as closest match in the data base. This germ line gene encodes residues 1-95 of the target antibody (FIG. 6, top row of alignment). All clones have a Y49F mutation at position 49, probably introduced into the light chain gene by somatic hypermutation during B cell differentiation.

In order to verify the N-terminus of the obtained light chain sequence, additional PCR reactions were performed with a forward primer annealing to the secretion signal of germ line gene Vk19-17 and a reverse primer specific for the CDR3 in the derived clones (FIG. 6, positions 89-97), or with the kappa specific reverse primer used in the initial PCR reactions.

```
LC          mVk19-17_leadF: ATGGAGTCACAGATTCAGGTCTTTG
primer sequence  (SEQ ID NO: 7)
            BAP015_LC_CDR3_R: CCGAACGTGTACGGAGTACTATAATG
            (SEQ ID NO: 8)

HC          mVHJ558_F: CAGGTCCAGCTGCAGCAG (SEQ ID NO: 9)
primer sequence  BAP015_HV_CDR3_R: CCCCAGTAAGCAAACCGACTTG
            (SEQ ID NO: 10)
```

Both primer combinations resulted in a PCR product of the expected size (FIG. 7). The LC variable domain was amplified with 2 primer combinations (lanes 1 and 2), and the HC variable domain was amplified using 4 primer combinations (lanes 3-6). Expected sizes of PCR products were ~330 bp (lanes 1, 3, 4) and ~500 bp (lanes 2, 5, 6), respectively. PCR products were gel purified, TOPO-TA cloned and sequenced (6 clones each). Both PCR reactions amplified the same light chain variable domain. The obtained DNA and deduced amino acid sequence is shown FIG. 8 (SEQ ID NO: 5). Only a single productive light chain sequence was amplified from the provided Hybridoma cell line. Mouse germ line gen Vk19-17 was identified as closest match. CDR residues are shown in bold.

2) Heavy Variable Domain

Sequence analysis revealed that primer H4 amplified a non-productive rearranged heavy chain (FIG. 9). The identified sequence is derived from a non-productive V-D-J recombination originating probably from germline gene Vh14-3*2. Fragment D is out of frame creating a stop signal in the CDR 3 region.

Primer combinations H1, H2, H3, H5, H6, and H7 amplified the same heavy chain variable domain, derived from germ line gene Vh1-4*1 (FIG. 10). All primer combinations amplify the same heavy chain variable domain, derived from germ line gene Vh1-4*1. Only sequence differences to Vh1-4*1 are shown. The sequence variations in the first 10 amino acids are caused by ambiguities in the PCR primers. Amino acid changes in individual clones (e.g. pos. 14, pos. 33, pos. 58, pos. 88 and pos. 98) are probably created during PCR.

Additional PCR reactions with gene specific primers were performed in order to verify the obtained HC variable domain sequence. The resulting PCR products were TOPO-TA cloned and sequenced. All clones had the exact same sequence (FIG. 11, SEQ ID NO: 6). Only a single productive heavy chain sequence was amplified from the provided Hybridoma cell line. Mouse germ line gen Vh1-4*1 was identified as closest match. CDR residues are shown in bold.

Example 3

Preparation of Anti-EMAPII Chimeric Antibody (1) Cloning of Anti-EMAPII Chimeric Antibody-Subcloning of Fab Domain of Light Chain in Human Kappa Fc Region and of Fab Domain of Heavy Chain in Human Ig G1 Fc Region The variable domains of the obtained murine (mouse) anti-EMAPII antibody were cloned into mammalian expression system pBAK2b which is commercially available from Bio-Atla.

The light chain variable domain was fused in frame to a human kappa constant region; the heavy chain variable domain was fused in frame to a human IgG1 constant region. Both genes are preceded by a leader peptide for secretion of full length IgG1 antibodies into the medium.

Five clones were sequenced to confirm the integrity and sequences of LC and HC reading frames in the expression vector. Three clones were selected for expression tests in CHO cells.

Glycerol stocks of the three clones were prepared and endotoxin-free plasmid DNA was prepared for expression tests in CHO cells.

(2) Quantification of Chimeric IgG1 after Transfection into CHO Cells

The plasmid DNA obtained as described above was transfected into CHO-S cells. One week before transfection, CHO-S cells (CD-CHO: Invitrogen, 10743-029) were transferred into monolayer culture in serum-supplemented DMEM (Dulbecco's Modified Eagle Medium: Invitrogen, 11965-092). One day before transfection, $0.4 \times 10^5$ cells were plated into 100 µl serum-supplemented DMEM in a 96-well format for each transfection sample. A DNA-lipofectamine complex was prepared for each transfection sample. For this purpose, 0.2 µg of DNA was diluted in 25 µl of Opti-MEM reduced serum medium. 0.5 µl of lipofectamine (lipofectamine 2000: Invitrogen, 11668-027) was diluted in 25 µl of Opti-MEM reduced serum medium. The lipofectamine dilution was incubated at room temperature for 5 minutes. The diluted DNA and the diluted lipofectamine were mixed with each other, and then incubated at room temperature for 20 minutes. 50 µl of the resulting DNA-lipofectamine complex was added to each well containing the cells and the medium, and the content of each well was lightly mixed. Then, the cells were incubated overnight in a 5% $CO_2$ incubator at 37° C. The medium in each well was removed by suction, and 100 µl of serum-supplemented DMEM was added to each well. 48 hours after transfection, the cell culture supernatant was collected, and the concentration of recombinant chimeric IgG in the cell culture supernatant was determined by ELISA. The recombinant chimeric IgG in the cell culture supernatant was captured using an anti-human Fc antibody immobilized on a plate. The bound chimeric IgG was detected using an anti-human IgG HRP conjugate and quantified using commercial human IgG as a standard.

In brief, each well of a Nunc-Immuno Maxisorp 96-well plate (Nalge Nunc, 439454) was coated with 100 µl of a coating solution containing 10 µg/µl of affinity-purified Fc-specific goat anti-human IgG (Sigma, 12136-1 ml). The plate was sealed and incubated overnight at 4° C. Each well of the plate was washed with 200 µl of washing buffer with stirring at 200 rpm at room temperature for 5 minutes. 200 µl of blocking buffer was added to each well of the plate, and the plate was stirred at 200 rpm at room temperature for 1 hour. 100 µg of purified human serum IgG (Invitrogen, 12000 C) in 1 µl of blocking buffer was added in duplicate to each well of the plate. 100 µl of the supernatant resulting from the transfection process was added in duplicate to each well of the plate. Then, the plate was stirred at 200 rpm at room temperature for 1 hour. Each well of the plate was washed twice with 200 µl of washing buffer at 200 rpm at room temperature for 5 minutes. 100 µl of a 1:5000 dilution of HRP-conjugated affinity-purified goat anti-human antibody (Promega, W4031) in blocking buffer was added to each well of the plate. The plate was stirred at 200 rpm at room temperature for 1 hour, after which each well was washed three times with 200 µl of washing buffer at 200 rpm at room temperature for 5 minutes. TMB substrate (Sigma) was added to each well, and then the plate was incubated at room temperature. 100 µl of 1N HCl was added to each well to terminate the reaction. Then, each well was read at 450 nm.

(3) Comparison of Affinity of Monoclonal Antibody with Chimeric Antibody

1) Optimization of ELISA

Figure 12:
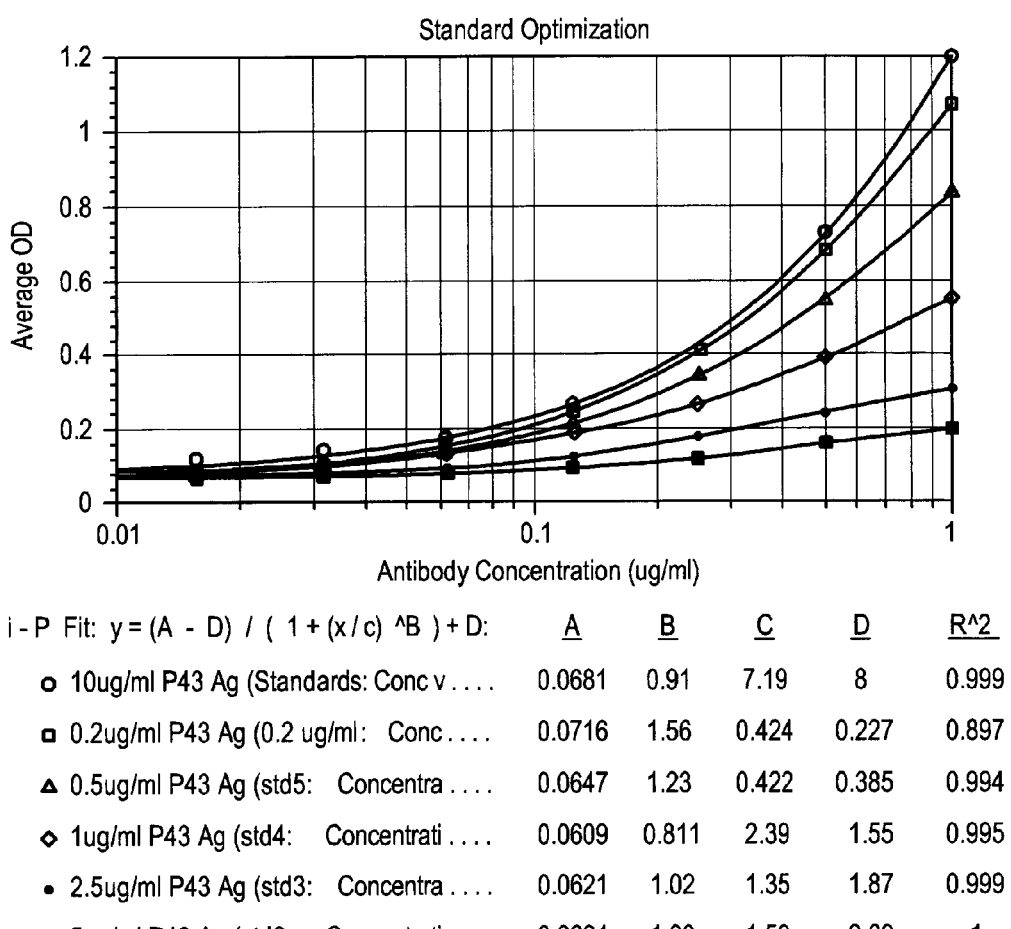
FIG. 12 is a graph showing the results of determining the optimized ELISA conditions of mouse anti-EMAPII antibody.

In order to identify the linear range for testing the antigen binding of the murine and chimeric clones, a matrix experiment was set up as follows:

Wells of a 96 well plate were coated with 100 µl of different concentrations of EMAPII antigen (10 µg/ml, 5 µg/ml, 2.5 µg/ml, 1 µg/ml, 0.5 µg/ml, 0.2 µg/ml) and were incubated at 37° C. for 2 hours. The coated antigens were blocked using BSA and washed with washing buffer. Dilutions of the parental murine anti-EMAPII antibody (starting at 1 µg/ml, two-fold serial dilution) were added to the antigens and incubated for 2 hours. The mixture was washed three times and anti-IgG-HRP antibody was added to the mixture and incubated for 1 hour. The mixture was washed with washing buffer three times. The substrate was added to the mixture and maintained for 30 minutes. After developing, stop solution was added and detected absorbance at the wavelength of 450 nm (FIG. 12). Bound antibody was detected with anti-mouse IgG-HRP conjugate. A concentration of 2.5 µg/ml antigen was selected for testing the chimeric clones.

2) Comparison of Affinity

Figure 13:
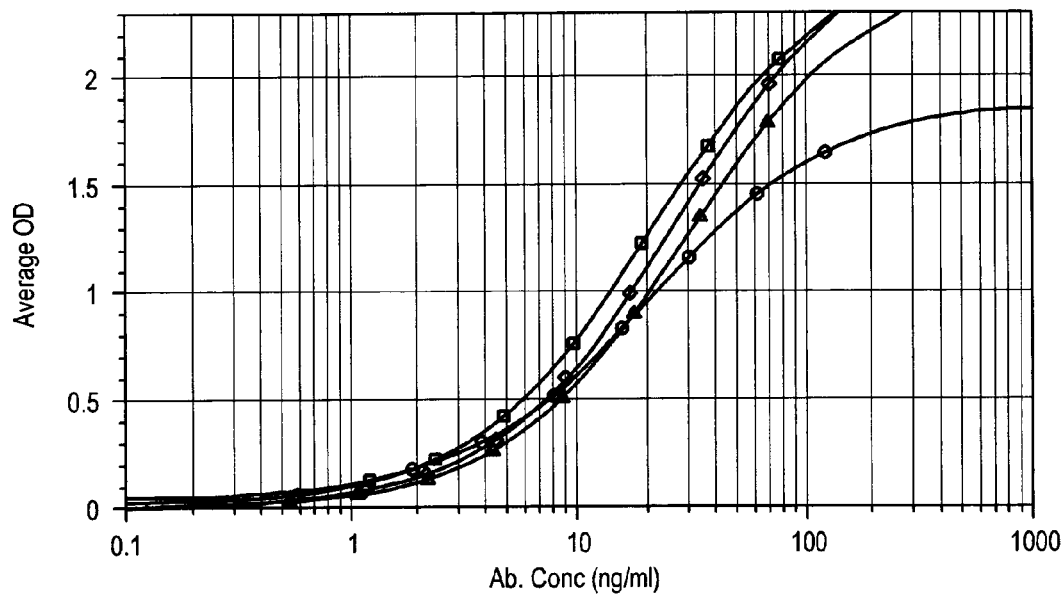
FIG. 13 is a graph showing the binding affinity of chimeric anti-EMAPII antibody in comparison with that of mouse anti-EMAPII monoclonal antibody.

The ability of mouse/human chimeric antibody BAP015_1 to bind to the EMAPII antigen was determined by using the ELISA protocol provided by StemScience and the optimized conditions determined as described above. Bound chimeric antibody was detected with anti-human-IgG HRP conjugate (FIG. 13). All 3 clones tested bind to EMAPII. The binding curves of all 3 clones are very similar to each other and to the murine antibody.

The murine EMAPII mAb reached 50% binding saturation at 20.9 ng/ml (FIG. 13). The chimeric antibody reached 50% binding saturation at 21.5-30.2 ng/ml. Taken all assay variations into account, the data indicate that the chimeric antibody binds with very similar affinity to the target EMAPII antigen as the original murine mAb.

Example 4

Humanization of Anti EMAPII Chimeric Antibody (1) Cloning of Fab Domain of Heavy and Light Chain (Full Length) in Human Library 1) Construction of Humanized Variable Domains Double stranded DNA fragments coding for the light chain and heavy chain CDR sequences from chimeric clone BAP015_1 (SEQ ID NOs. 11 and 19) were combined with BioAtla proprietary pools of human frameworks. Full length variable domains were then cloned into BioAtla's proprietary mammalian expression system pBAK2.

Light chain variable domains were cloned in frame with a secretion signal and a human kappa constant domain. Heavy chain variable domains were cloned in frame with a leader sequence and a human IgG1 constant domain. The library of humanized variants was frozen as glycerol stock.

2) Manufacturing of Plasmid DNA after Transformation of *E. coli*

Aliquots of the humanized library were plated and single colonies arrayed into to 96 well plates. Each plate also contained 3 wells with positive control (BAP015_1) and negative control (vector only). Cultures were grown over night and plasmid DNA was prepared for transfection.

3) Transfection of Humanized Library

CHO S cells were seeded in 96-well plates and transfected with mini-prepped DNA of the humanized clones. Specific method was the same as the transfection method as described in the above (example 3-(2)).

4) Culture and Measurement of Ig G

Cell culture supernatant was collected at 48 hours after transfection and IgG concentration for each humanized clone and the controls was determined using BioAtla ELISA protocol for quantification of human IgGs as described for the chimeric antibody (example 3-(2)).

Figure 14:
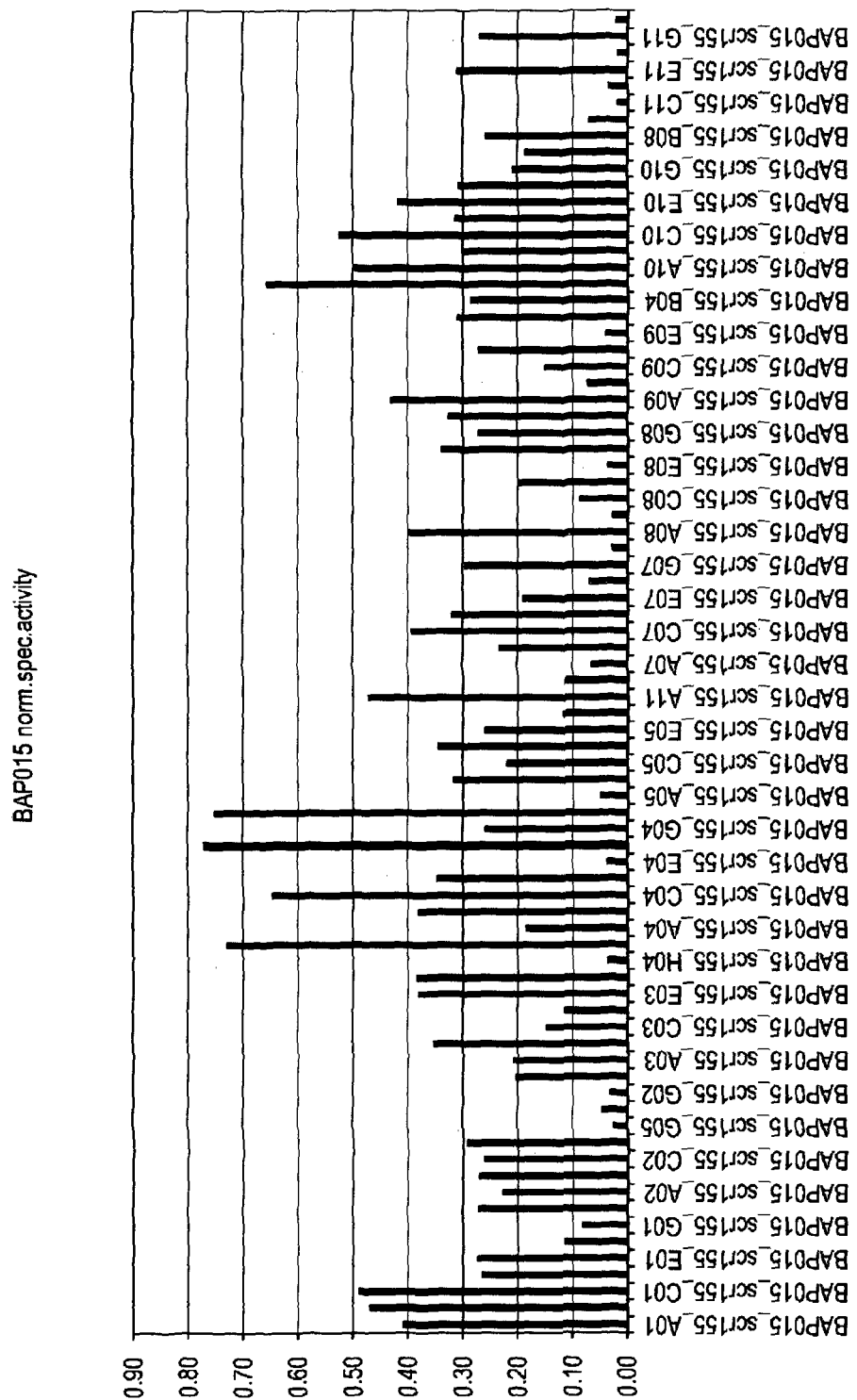
FIG. 14 is a graph showing the specific activities of recombinant humanized clones to antigen.
Figure 15:
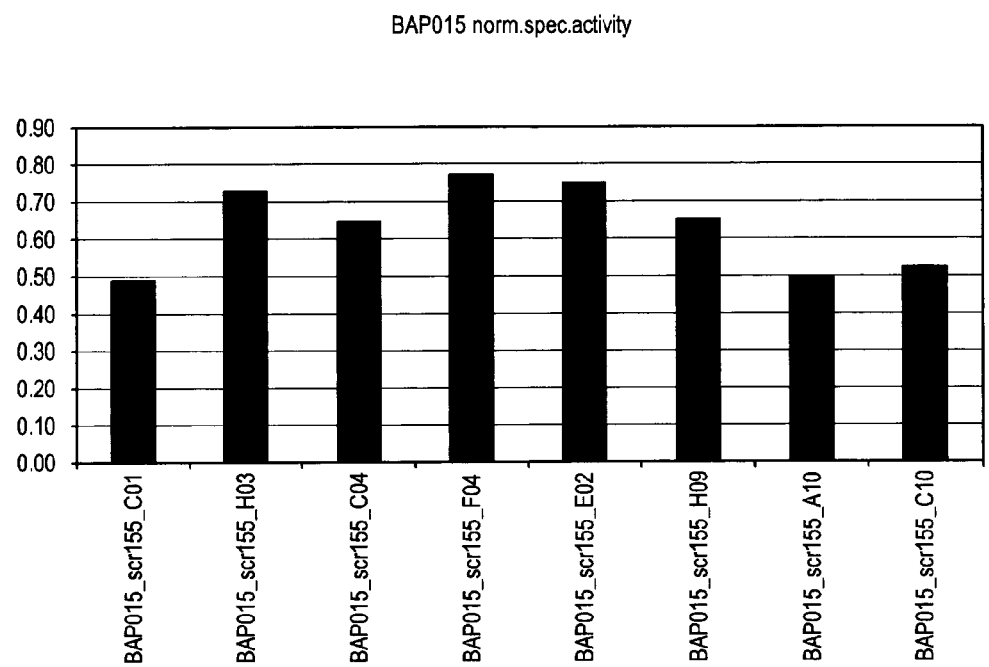
FIG. 15 is a graph showing the specific activities of the selected 1st HITs.

5) Measurement of Activity Using ELISA—Selection of Candidate, Screening of Humanized Library Binding of the humanized clones to antigen EMAPII was tested in parallel using the antigen and protocol provided by Stemsciences. Specific method was the same as described in the above (example 3). Specific activity (affinity/quant) was calculated for each clone and compared to the average specific activity of the positive control (chimieric clone BAP015_1) on the same plate. Clones with low expression levels were filtered out for selecting the primary hits. Clones with low expression levels (lower than BAP015_1) and low binding activity were filtered out for selecting the primary hits (candidates having effects of significance are referred to as 'hit'). Data from plate BAP015_scr155 are shown as an example in FIGS. 14 and 15. The top hits from each plate were selected for confirmation and screened again.

(2) Comparison of Affinity of Candidate and Analysis of Protein Sequence

1) Confirmation Screen

The top hits from each plate were re-arrayed, re-transfected into CHO-S and screened in duplicates as described above. The top 7 clones (BAP015hum01-BAP015hum07; respectively, in order, a pair of one of light chain variable domain sequences (SEQ ID NOs. 12 to 18) and one of heavy chain variable domain sequences (SEQ ID NOs. 20 to 26)) were selected for additional confirmation screenings.

Figure 16:
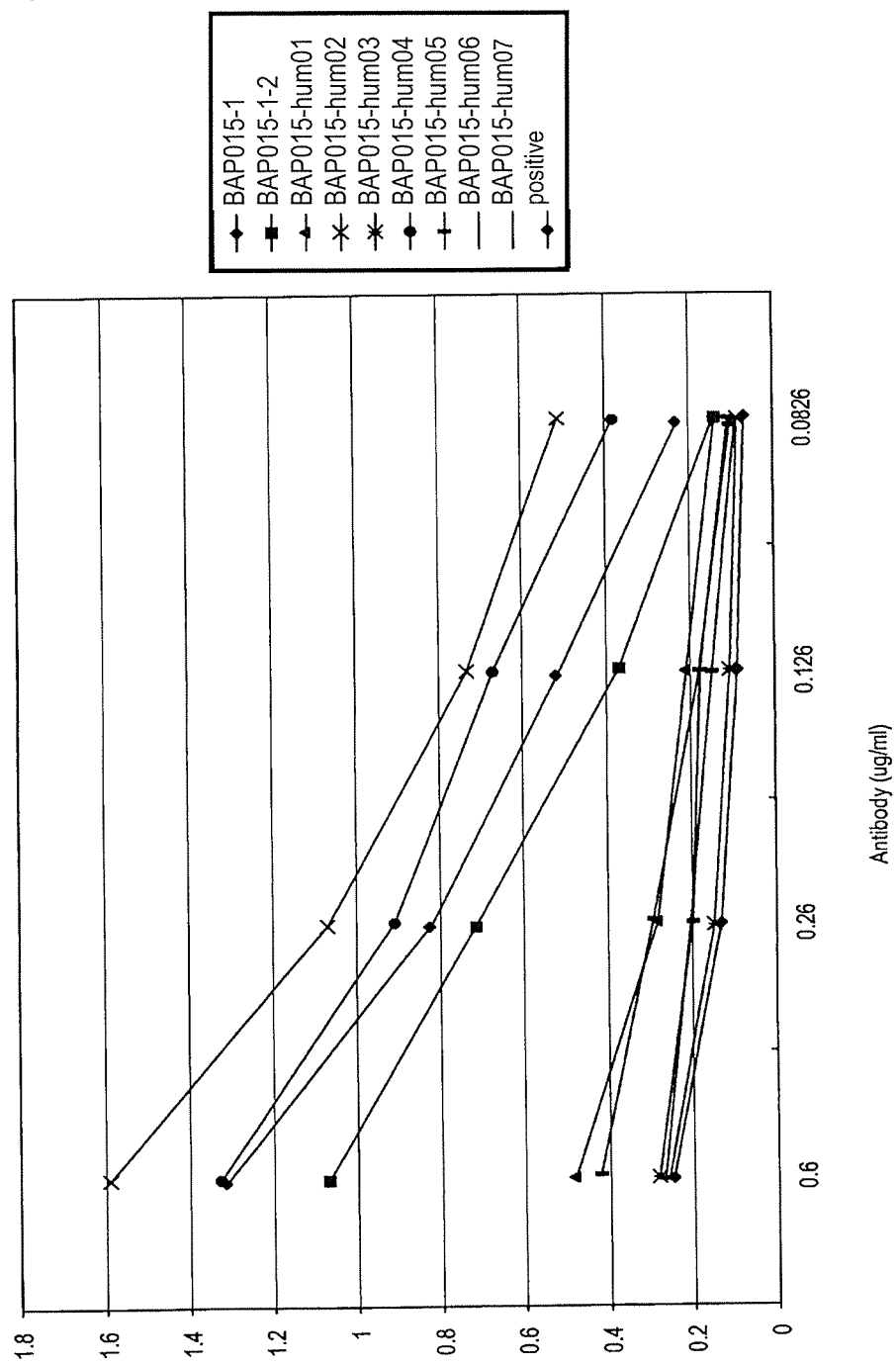
FIG. 16 is a graph showing the specific activities of top HITs to antigen.

Dilutions of each antibody (1:50 to 1:100 for antigen binding; 1:200 and 1:400 dilutions were used for quant ELISA) were assayed for antigen binding in duplicates. For comparison, the same experiment was performed using chimeric antibodies (BAP015-1, BAP015-2) and mouse monoclonal antibody (positive). Specific activity for each dilution was calculated and the average specific activity for each clone was shown in FIG. 16.

2) Sequencing

Figure 17:
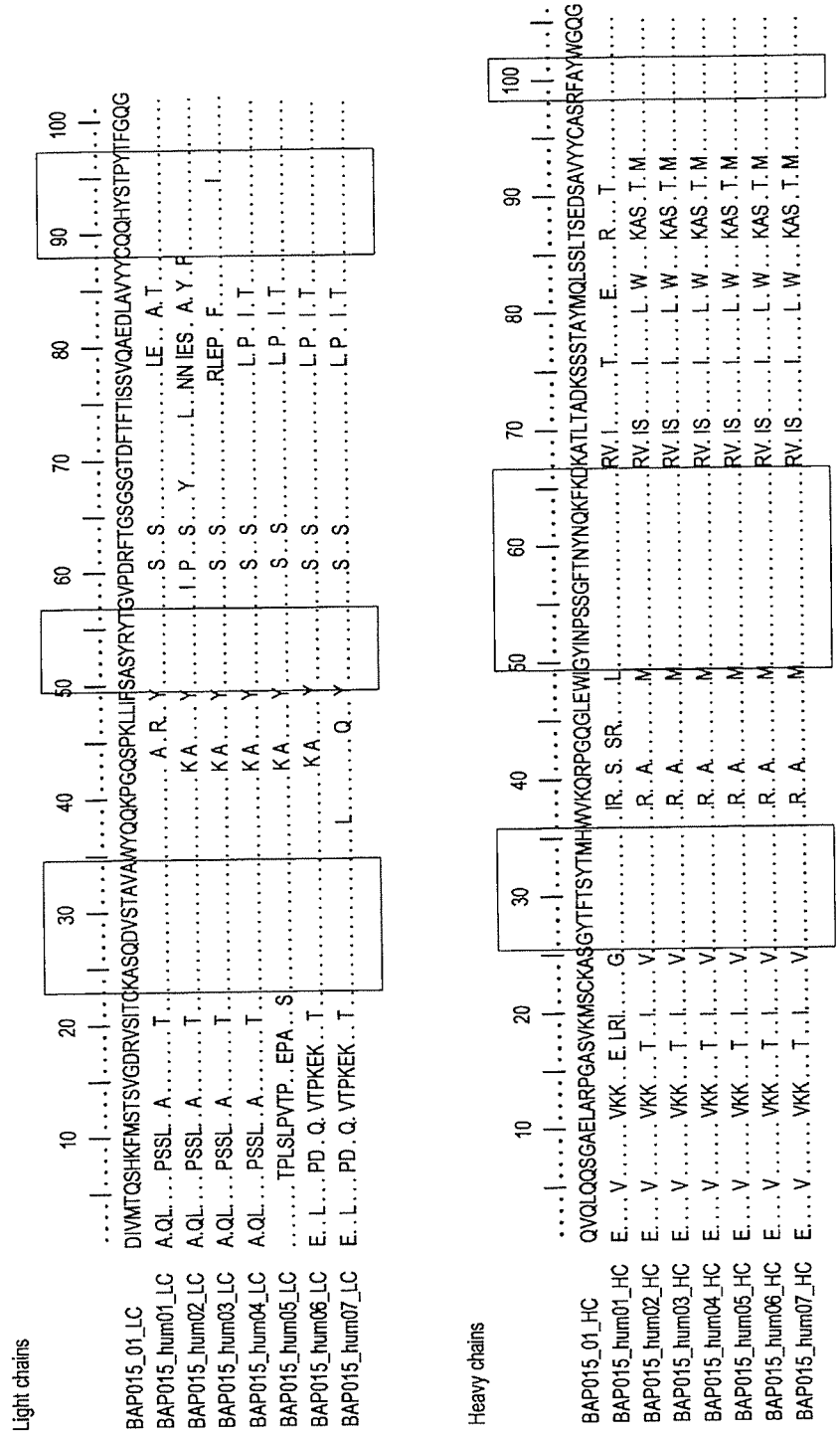
FIG. 17 shows the amino acid sequences of humanized anti-EMAPII antibodies of seven top HITs among recombinant humanized clones (SEQ ID NOS: 11-18 (Light chains) and SEQ ID NOS: 19-26 (Heavy chains)).

The light and heavy chain variable domains of the top 7 clones were sequenced, and the deduced amino acid sequences were aligned and compared to each other and to the mouse variable domains in clone BAP015_1. Each of the 7 top hits has a unique light chain (FIG. 17). Hits BAP015-hum01 to 04 share the same framework 1 sequence and hits BAP015-hum06 and 07 share the same framework 1 sequence. BAP015-hum02 to 06 share the same frame work 2 sequence. Clones BAP015-hum04 to 07 share the same frame work 3 sequence. An alignment of the heavy chain variable domains is shown in FIG. 17. Only 2 different heavy chains were identified in the top humanized hits. The light chain CDRs and the heavy chain CDRs are boxed. The top 7 humanized hits contain 7 unique light chains and 2 unique heavy chains.

The invention claimed is:

1. A humanized anti-EMAPII (endothelial monocyte activating polypeptide II) antibody, comprising:
   (i) a light-chain variable domain having an amino acid sequence set forth in any one of SEQ ID NO: 12 to SEQ ID NO: 18; and
   (ii) a heavy-chain variable domain having an amino acid sequence set forth in any one of SEQ ID NO: 20 to SEQ ID NO: 26.

2. The humanized anti-EMAPII antibody of claim 1, wherein the humanized anti-EMAPII antibody comprises a pair of a light-chain variable domain and a heavy-chain variable domain selected from the group consisting of a light-chain variable domain having an amino acid sequence set forth in SEQ ID NO: 12, and a heavy-chain variable domain having an amino acid sequence set forth in SEQ ID NO: 20; a light-chain variable domain having an amino acid sequence set forth in SEQ ID NO: 13, and a heavy-chain variable domain having an amino acid sequence set forth in SEQ ID NO: 21; a light-chain variable domain having an amino acid sequence set forth in SEQ ID NO: 14, and a heavy-chain variable domain having an amino acid sequence set forth in SEQ ID NO: 22; a light-chain variable domain having an amino acid sequence set forth in SEQ ID NO: 15, and a heavy-chain variable domain having an amino acid sequence set forth in SEQ ID NO: 23; a light-chain variable domain having an amino acid sequence set forth in SEQ ID NO: 16, and a heavy-chain variable domain having an amino acid sequence set forth in SEQ ID NO: 24; a light-chain variable domain having an amino acid sequence set forth in SEQ ID NO: 17, and a heavy-chain variable domain having an amino acid sequence set forth in SEQ ID NO: 25; and a light-chain variable domain having an amino acid sequence set forth in SEQ ID NO: 18, and a heavy-chain variable domain having an amino acid sequence set forth in SEQ ID NO: 26.

3. The humanized anti-EMAPII antibody of claim 1, wherein the humanized anti-EMAPII antibody further comprises an IgG1 human constant domain.

4. A pharmaceutical composition, comprising the humanized anti-EMAPII antibody of claim 1.

5. A pharmaceutical composition for treating Alzheimer's Disease, comprising the humanized anti-EMAPII antibody of claim 1.

6. A kit for quantification of EMAPII, comprising a humanized anti-EMAPII antibody of claim 1.

7. A nucleic acid molecule encoding a light-chain variable domain having an amino acid sequence set forth in any one of SEQ ID NO: 12 to SEQ ID NO: 18.

8. A nucleic acid molecule encoding a heavy-chain variable domain having an amino acid sequence set forth in any one of SEQ ID NO: 20 to SEQ ID NO: 26.

9. A recombinant vector, comprising nucleic acid molecules encoding a light-chain variable domain having an amino acid sequence set forth in any one of SEQ ID NO: 12 to SEQ ID NO: 18 and/or heavy-chain variable domain having an amino acid sequence set forth in any one of SEQ ID NO: 20 to SEQ ID NO: 26.

10. A transformed cell, comprising the recombinant vector of claim 9.

11. A method of producing a humanized anti-EMAPII antibody, comprising culturing the transformed cell of claim 10 under conditions whereby the humanized anti-EMAPII antibody is expressed.

12. A method of treating Alzheimer's Disease, comprising administering a humanized anti-EMAPII antibody of claim 1.

13. A chimeric anti-EMAPII antibody, comprising:
a light-chain variable domain having an amino acid sequence set forth in SEQ ID NO: 11; and
a heavy-chain variable domain set forth in SEQ ID NO: 19.

14. A pharmaceutical composition for treating Alzheimer's Disease, comprising a humanized anti-EMAPII antibody of claim 2.

15. A pharmaceutical composition for treating Alzheimer's Disease, comprising a humanized anti-EMAPII antibody of claim 3.

16. A method of treating Alzheimer's Disease, comprising administering a humanized anti-EMAPII antibody of claim 2.

17. A method of treating Alzheimer's Disease, comprising administering a humanized anti-EMAPII antibody of claim 3.

18. A method of treating Alzheimer's Disease, comprising administering a pharmaceutical composition of claim 4.

19. A method of treating Alzheimer's Disease, comprising administering a pharmaceutical composition of claim 5.

20. The humanized anti-EMAPII antibody of claim 2, wherein the light-chain variable domain has the amino acid sequence set forth in SEQ ID NO: 13, and the heavy-chain variable domain has the amino acid sequence set forth in SEQ ID NO: 21.

* * * * *